US007067104B2

(12) United States Patent
Sandhage

(10) Patent No.: US 7,067,104 B2
(45) Date of Patent: Jun. 27, 2006

(54) SHAPED MICROCOMPONENT VIA REACTIVE CONVERSION OF BIOLOGICALLY-DERIVED MICROTEMPLATES

(75) Inventor: Kenneth H. Sandhage, Upper Arlington, OH (US)

(73) Assignee: The Ohio State University, Columbus, OH (US)

( * ) Notice: Subject to any disclaimer, the term of this patent is extended or adjusted under 35 U.S.C. 154(b) by 331 days.

(21) Appl. No.: 10/158,582

(22) Filed: May 30, 2002

(65) Prior Publication Data

US 2003/0099763 A1 May 29, 2003

Related U.S. Application Data

(60) Provisional application No. 60/294,447, filed on May 30, 2001.

(51) Int. Cl.
*C01B 13/14* (2006.01)
(52) U.S. Cl. .............. 423/592.1; 423/69; 423/111; 423/155; 423/179; 423/335; 423/1; 501/154; 501/1; 977/1
(58) Field of Classification Search .............. 977/1; 423/325, 335, 339, 155, 179, 111, 69
See application file for complete search history.

(56) References Cited

U.S. PATENT DOCUMENTS 3,929,971 A * 12/1975 Roy ........................ 423/308
4,039,726 A * 8/1977 Carr et al. ................ 428/700

OTHER PUBLICATIONS

Parkinson et al, Nanotechnology, vol. 17, No. 5, 1999, pp. 190-196.*

Letic-Gavrilovic et al, Dental Materials Journal, vol. 19, No. 2, 2000, pp. 99-132.*
Minerals.net, "Corundum," http://minerals.net/mineral/oxides/corundum/corundum.htm accessed Dec. 3, 2004.*
Lowenstam et al., Mineralization by Organisms and the Evolution of Biomineralization, *Biomineralization and Biological Metal Accumulation: Biological and Geological Perspectives*, Papers presented at the Fourth International Symposium on Biomineralization, Renesse, The Netherlands, Jun. 2-5, 1982.
Brott, et al., Ultrafast holographic nanopatterning of biocatalytically formed silica, *Nature*, 413, 291-293 (2001).
Kröger, et al., Polycationic Peptides from Diatom Biosilica That Direct Silica Nanosphere Formation, *Science*, vol. 285, Nov. 5, 1999.
Coradin et al., ChemBioCHem, 2003, vol. 4, pp. 251-259.
Knecht et al., Langmuir, 2004, vol. 20, pp. 4728-4732.

* cited by examiner

Primary Examiner—Leon B. Lankford, Jr.
Assistant Examiner—Allison M. Ford
(74) Attorney, Agent, or Firm—Standley Law Group LLP

(57) ABSTRACT

The present invention is focused on a revolutionary, low-cost (highly-scaleable) approach for the mass production of three-dimensional microcomponents: the biological reproduction of naturally-derived, biocatalytically-derived, and/or genetically-tailored three-dimensional microtemplates (e.g., frustules of diatoms, microskeletons of radiolarians, shells of mollusks) with desired dimensional features, followed by reactive conversion of such microtemplates into microcomponents with desired compositions that differ from the starting microtemplate and with dimensional features that are similar to those of the starting microtemplate. Because the shapes of such microcomponents may be tailored through genetic engineering of the shapes of the microtemplates, such microcomposites are considered to be Genetically-Engineered Materials (GEMs).

28 Claims, 18 Drawing Sheets

SHAPED MICROCOMPONENT VIA REACTIVE CONVERSION OF BIOLOGICALLY-DERIVED MICROTEMPLATES

RELATED APPLICATION DATA

This application claims the priority benefit of U.S. Provisional Patent Application Ser. No. 60/294,447 filed May 30, 2001, which is hereby incorporated herein by reference.

TECHNICAL FIELD OF THE INVENTION

The present invention is in the field of shaped microcomponents fabricated via the reactive conversion of biologically-derived microtemplates. The microtemplate may possess a shape that is naturally occurring, one that is modified through genetic engineering or one that is obtained through the use of a biocatalyst, or combinations thereof.

BACKGROUND OF THE INVENTION

The worldwide research and development effort on microdevices (e.g., electromechanical, hydromechanical, thermomechanical, electrochemical, thermoelectrical, etc.) has increased dramatically over the past decade. Such devices have found significant use as sensors in automotive and medical applications, with estimates of the global MEMS (microelectromechanical systems) market ranging from $12–14 billion in 2000. However, a far larger untapped potential exists for the use of new micromechanical devices in a variety of advanced applications, such as in: i) medicine (e.g., targeted drug or radiation delivery, rapid clinical and genomic analyses, in vitro sensors, microtools for surgery, micropumps and microvalves, microreactors, microcomponents used in biomedical imaging, etc.), ii) transportation and energy production (e.g., new sensors and actuators for pollution control, enhanced energy utilization, and improved engine performance; microcomponents for automotive, diesel, jet, or rocket engines; microcomponents for turbines used in energy conversion or generation; microreactors, micropumps, microbearings, etc.), iii) communications and computing (e.g., micro-optical devices, microactuators, microswitches, microtransducers, etc.), iv) the production/manufacturing of food, chemicals, and materials (e.g., micro-robotics, rapid on-line microsensors, microreactors, micropumps, microdies, etc.), and a variety of other consumer products (e.g., for lighting, portable electrical devices, etc.).

Despite the recognized technological and economic significance of new microdevices, the commercial fabrication methods used to date have been largely limited to techniques developed within the microelectronics industry (e.g., mlcromachining of silicon by photolithographylchemlcal etching; reactive ion etching; x-ray lithography/electroplating, etc.). While appropriate for the manufacturing of planar electronIc devices, such methods are not well suited for the rapId, low-cost mass production of three-dimensional microcomponents with complex, non-planar geometries. Furthermore, the properties of silicon (room temperature brittleness, poor creep resistance at [$\geq 600°$ C.] greater than or eaual to 600° C., high thermal conductivity, modest melting paint, biochemical incompatibility, etc.) make silicon-based microdevices unattractive for a number of potential applications. New fabrication methods capable of yielding self-assembled, non-silicon microdevices in a massively parallel fashion are needed to allow for a much wider range of commercial applications.

A significant level of worldwide activity has been undertaken to develop genetically-engineered drugs or plants. However, relatively little work has been conducted to date to develop "Genetically-Engineered Materials" ("GEMS"). That is, research and development is lacking on the use of biological systems to mass produce microcomponents or microdevices comprised of advanced materials with very controlled, fine-scale, 3-dimensional structures in a very inexpensive, reproducible manner. The purpose of the present invention is to provide a novel approach for converting 3-dimensional, biologically-derived micro- and nano-templates into new materials with a retention of shape/dimensions and morphological features. The ultimate objective of this approach is to mass-produce micro- and nano-templates of tailored shapes through the biological reproduction of naturally-occurring or genetically-tailored organisms, and then conversion of such templates by controlled chemical reaction(s) into near net-shaped, micro- and nano-components of desired compositions. In other words, the goal is to develop a new process that utilizes a unique combination of the attractive features of biological systems (e.g., the low-cost culturing of biological organisms for the rapid mass production of templates with precise retention of naturally-occurring or genetically-tailored shapes and surface features), and/or genetic engineering (e.g., the versatile tailoring of genomes of biological organisms capable of producing templates with a wide variety of shapes, dimensions, and surface features); and net-shape reaction processing (e.g., for the conversion of mass-produced, biologically-derived templates into near net-shaped components comprised of new materials with enhanced properties for a given application).

Certain biological systems are capable of reproducibly generating complex micro- and nano-scaled assemblies with a high degree of precision. An example of a biological system with very reproducible, yet complex and fine shapes and morphologies is the diatom *Bacillariophyceae*. Diatoms are "microscopic (1–500 micrometers in length) single-celled algae with characteristic rigid cell walls (frustules) compose of amorphous silica" (from a paper by J. Parkinson, R. Gordon entitled "Beyond Micromachining: The Potential of Diatoms," *Trends in Biotechnology*, Volume 17, Number 5, pp. 190–196, 1999) (hereby incorporated by refernce). Diatoms exist in large numbers in a variety of aquatic environments and are believed to account for about 25% of the world's annual production of primary carbon. Diatoms have been classified on the basis of the shape of the silica frustule, with each species of diatom exhibiting a particular, reproducible frustule shape. Two general frustule shape categories are: 1) centric diatoms that have radially-symmetric frustules, and 2) pennate diatoms that are elongated and tend to have parallel rows of holes in the silica frustule, with the rows of holes tending to be oriented perpendicular to the elongated axis. Some diatom species also exhibit patterned arrangements of multiple frustules (e.g., helical-shaped clusters of frustules). In addition to having particular frustule shapes with sizes typically ranging from about 1 to about 500 micrometers in length, the diatoms have very complex, reproducible, fine (submicron) surface features (pores, ridges, nodules, protuberances, etc.). For example, the spacing between rows of pores in a diatom frustule typically may be only about 0.3 to 2 micrometers, depending on the diatom species. The pores in the frustule wall may also be on the order of 100 nanometers (0.1 micrometers) in diameter or smaller. Furthermore, the walls of diatom frustules are comprised of nanospheres (typically about $10^1$–$10^2$ nm in diameter).

Parkinson and Gordon have recently discussed the attractive benefits of using diatoms as materials or microcomponents for certain applications (*Trends in Biotechnology*, Volume 17, Number 5, pp. 190–196 (1999). Although the reproduction rate of diatoms varies with species and environmental conditions (e.g., temperature, nutrient concentration, concentration of the silicon source, etc.), typical reproduction rates range from 1 to 8 times per day. Since asexual reproduction results in repeated doubling of the number of diatoms (2 to 4 to 8 to 16 . . . etc.), such a reproduction rate may yield large numbers of diatoms in a relatively short time (e.g., billions of diatoms within a few weeks). For example, at a reproduction rate of three times per day, the number of similarly-shaped frustules generated in ten days would exceed 1 billion (30 doublings=$2^{30}$=1,073,741,824). The combination of asexual and sexual reproduction results in diatom frustules of similar shape with a relatively narrow distribution of sizes. The variation in surface features (e.g., pore sizes, spacing between pores) may be even smaller. Once the relevant biochemistry and genetic code is understood for the shapes of diatom frustules and, in particular, how such a code may be altered to produce desired (tailored) frustule shapes and features, then shape-tailored diatom frustule templates could be produced at low cost, in large quantities, and in very reproducible shapes and very fine geometries. Control of features at submicron and nanometer dimensions would be possible while achieving economy of scale. Such a high rate of reproduction of self-assembling, complex three-dimensional shapes is an inherent biological characteristic that is highly attractive from a manufacturing perspective.

Given the wide natural variations observed in the shapes and surface features of diatom frustules, genetic engineering may be used to produce a wide variety of tailored frustule shapes (e.g., microtubes, microgears, microwheels, micropins, microsprings, microrotors, microballs, microsyringes, microcapsules, etc.). In other words, the fact that there are an estimated 100,000 species of diatoms, with each species possessing a unique frustule shape, allows new, non-deadly genetic modifications may be made to existing diatoms, so as to produce new living diatoms that possess frustules with new shapes that are appropriate for desired applications. With the understanding of the biochemistry and genetic factors responsible for the diatom shape, genetic engineering may be used to produce diatom frustules with an even wider variety of complex shapes, dimensions, and surface features than are currently available in nature. Biological reproduction (which may involve cloning) of a genetically-tailored diatom cell may then be used to generate large numbers of similar shape-tailored frustules.

Biochemical mechanisms responsible for the formation of diatom frustules are becoming better understood. Kroger, et al. (*Science*, Volume 286, pages 1129–1132, Nov. 5, 1999; Proceedings of the National Academy of Science of the USA, Volume 97, Number 26, pages 14133–14138, Dec. 19, 2000) (incorporated herein by reference) have recently isolated polypeptides (called "silaffins") and polyamines within the wall of a diatom (*Cylindrotheca fusiformis*). Silaffins have been found to be responsible for the precipitation of the silica nanoparticles within the frustule wall. Indeed, when these authors exposed a solution of silicic acid to a given silaffin, silica particles were rapidly formed by precipitation. Hence, silaffins are believed to act as biocatalysts for the precipitation of silica from seawater or fresh water environments. By varying the relative mixtures of silaffins and polyamines, along with solution pH, Kroger, et al. have been able to control the precipitation of silica from solutions of silicic acid, so as to produce spheres of varied diameter and with varied degrees of interconnectivity (i.e., ranging from loose, isolated microspheres or nanospheres to membranes of interconnected particles). These authors have also begun to identify the genomic sequences associated with these polypeptides and polyamines.

Recently, Brott, et al. (Nature, Volume 413, pages 291–293 (Sep. 20, 2001) (incorporated herein by reference) have generated silica/polymer composites with a well-controlled distribution of silica microspheres through the use of a patterned silaffin-derived biocatalyst. These authors prepared a solution containing a monomer and a 19-amino-acid peptide unit of a silaffin from the diatom *Cylindrotheca fusiformis*. They exposed this solution to a holographic laser pattern with alternating regions of high and low intensity. In the high intensity regions of the laser pattern, the monomer polymerized. Consequently, alternating rows of polymer and silaffin were produced with a pattern similar to that of the laser hologram. Subsequent exposure of this polymer/silaffin composite to a silicic acid solution resulted in the precipitation of silica particles and, hence, the formation of a polymer/silica composite with a pattern similar to that of the laser hologram. The well-controlled spacing of the silica particles in the layered silica/polymer composites allowed such composites to be used as optical diffraction gratings.

A significant current limitation in using diatom frustules for microdevices or microcomponents is the limited chemistry of the naturally-occurring frustules. Diatom frustules are comprised of amorphous, hydrated (opaline) silica. Although silica may be satisfactory for some microcomponents, silica has several unattractive characteristics, such as: 1) low toughness (i.e., silica being a brittle ceramic), 2) poor biocompatibility (e.g., silicosis, the tendency of fine silica to cause fibrosis of the lungs, may occur), 3) poor chemical compatibility upon exposure to basic oxides or basic oxide melts at high temperatures, 4) relatively low creep resistance at high temperatures (e.g., above about 1400° C. for pure, amorphous silica), 5) poor thermal cyclability (e.g., if amorphous silica is heated to a sufficient temperature and time so as to crystallize into quartz or cristobalite, then the resulting quartz or cristobalite will exhibit displacive transformations on heating and cooling with significant volume changes that are likely to result in cracking), and 6) poor resistance to erosion (e.g., from abrasive particles). Consequently, the porous amorphous silica in diatom frustules will not exhibit an appropriate combination of mechanical, thermal, biomedical, and chemical properties for a number of potential microdevice applications. Other examples of naturally-occurring microtemplates include the spicules of sponges (comprised of silica or calcium carbonate) and the shells of mollusks (comprised of calcium carbonate). Pure calcium carbonate also exhibits characteristics that are not attractive for a number of potential microcomponent applications, including: 1) low toughness, 2) poor high-temperature stability (i.e., $CaCO_3$ decomposes to CaO(s) and $CO_2$(g) at elevated temperatures), and 3) poor chemical compatibility upon exposure to acidic oxides or acidic oxide melts at high temperatures.

Accordingly, processing methods are needed that are capable of converting biologically-derived templates, such as silica microtemplates or calcium carbonate microtemplates, into microcomponents comprised of other materials with more appropriate and beneficial properties, while retaining the desired microtemplate shapes and fine (typically nanoscale) features.

Significant effort has been expended over the past several decades to develop low-cost methods for fabricating ceramic powders of varied composition that possess well-controlled size distributions. The rates of sintering and grain growth of ceramic powder preforms are strongly influenced by the size distribution of the ceramic powder. Hence, control over the powder size distribution is critical for fabricating ceramic bodies, or ceramic composite bodies, with controlled microstructures and shapes. Relatively little success has been achieved in developing methods for producing ceramic powders with controlled and complex shapes. New, low cost processing methods that are capable of producing ceramic powders with controlled and complex shapes, with controlled sizes, and with a variety of compositions are needed.

SUMMARY OF THE INVENTION

A principal object of the present invention is to obtain a biologically derived microtemplate with a desired shape and/or desired surface features, and then to convert the microtemplate into a different material through the use of shape-preserving chemical reactions. For example, a silica microtemplate with a desired shape may be obtained through the culturing of a naturally occurring diatom species with a frustule of desired shape or through genetic manipulation to yield a tailored frustule shape. A silica microtemplate with a desired shape may also be obtained by precipitation of silica with the use of a patterned biocatalyst, such as those that may be obtained derived from a diatom. The biocatalyst may be patterned in several ways. For example, the biocatalyst may be patterned via controlled phase separation from a liquid solution (e.g., with a holographic laser pattern). Alternately, the biocatalyst may be deposited in a desired pattern onto an inert substrate. Deposition methods include, but are not limited to, screen printing, photolithographic methods, direct writing from an ink jet, and direct writing from a fine solid tip coated with the biocatalyst. After patterning of the biocatalyst, the biocatalyst can be exposed to a silicon-bearing solution so as to generate a silica microtemplate with the same pattern as the biocatalyst. Such shaped silica microtemplates may then be converted into other oxides or oxide/metal composites through a chemical reaction with a fluid (liquid or gaseous) reactant. By proper choice of reactions, the converted (reacted) microtemplate (e.g., converted diatom frustule) may possess a composition, a shape, and surface features appropriate for a particular microcomponent or microdevice (e.g., microsprings, microball bearings, microsyringes, etc.). Hence, by this novel combined use of biology/genetic engineering and reaction engineering, a large number of microcomponents of desired shape and of desired composition may be produced.

The present invention includes a method for the production of shaped microcomponents comprising the steps of obtaining at least one biologically-derived microtemplate having an original chemical composition and an original dimensional feature; and subjecting the at least one biologically-derived microtemplate to a chemical reaction, so as to partially or completely convert the microtemplate into a microcomponent having a chemical composition different than the original chemical composition and having substantially the same dimensional feature(s) as the original biologically-derived microtemplate.

The microtemplate may be derived from a biocatalyst. As used herein, the term biocatalyst includes any biologically derived material used to catalyze the chemical formation of the microtemplate and/or otherwise facilitate physical phenomena required to bring about the formation of the microtemplate or shape the micortemplate, such as through transport phenomena, surface action, chelation, hydrogen bonding or other weak forces, adhesion, etc. The biocatalyst may be all or a portion of biologically derived materials that may be chemically catalytIc or physically shape-facilitating, such as proteins, nucleotides, polypeptides, lipoproteins, polysacchandes, etc. Thus, the biocatalyst may be all or a portion of a biologically-derived material from a natural organism or from a genetically-modified organism, whether or not chemically-modified.

These materials may be the result of genetic engineering or in vitro chemical modification or derivatization or physical processing or combinations thereof.

An example of such processing is the treatment of sili

Dimensional features includes shape or surface features. Surface features include, but are not limited to, pores, depressions, ridges, and protuberances. The dimensional features include, but are not limited to, a pore diameter, the spacing between pores, the length of a protuberance, the spacings between protuberances, the depth or width of a ridge, the spacings between ridges, the maximum length of a microtemplate, the minimum length of a microtemplate, the ratio of the maximum to minimum length of a microtemplate.

A microcomponent is defined as an object that may have at least one size dimension that is less than 1 millimeter and is preferably less than 100 microns and most preferably less than 25 microns and/or at least one surface feature with a dimension that is less than 1 millimeter and is preferably less than 100 microns and most preferably less than 25 microns.

The biologically-derived microtemplate may be selected from naturally-occurring microtemplates. A naturally-occurring microtemplate may be a hard or soft endoskeleton or exoskeleton, or a portion of a hard or soft endoskeleton or exoskeleton, generated by, or comprising part of, a once-living organism. The biologically-derived microtemplate may be produced by organisms selected from the group that includes, but is not limited to, Monera, Dinoflagellata, Haptophyta, Bacillariophyta, Phaeophyta, Rhodophyta, Chlorophyta, Zygnematophyta, Chrysophyta, Rhizopodea, Siphonophyta, Charophyta, Heliozoata, Radiolariata, Foraminifera, Mixomycota, Ciliophora, Basidiomycota, Deuteramycota, Mycophycophyta, Bryophyta, Tracheophyta, Porifera, Cnidaria, Platyhelminthes, Ectoprocta, Brachiopoda, Annelida, Mollusca, Arthropoda, Sipuncula, Echinodermata, and Chordata. Examples of naturally-occurring microtemplates include, but are not limited to, the frustules of diatoms (comprised of silica), dinoflagellates, silicoflagellates, ebridians, and radiolarians, the spicules of sponges (comprised of silica or calcium carbonate), the shells of mollusks (comprised of calcium carbonate), and intracellular crystals of bacterium (e.g., intracellular magnetite, $Fe_3O_4$, formed in magnetotactic bacterium). Other organisms that produce naturally-occurring microtemplates include, but are not limited to, other types of algae, mosses, molds, amoebas, worms, vertebrate, insects, jellyfishes, sea urchins, haptophytes, rhodophyta, and coccolithophores.

The biologically-derived microtemplate may be selected from non-naturally-occurring microtemplates. For example, the biologically-derived microtemplate may have a native shape that has been genetically altered so as to have a shape different from the native shape. Alternately, the microtemplate may have a shape that is obtained from a biologically-derived catalyst, or from a portion of a biologically-derived catalyst, or from a chemically-modified biocatalyst, or from a portion of a chemically-modified biocatalyst that has been patterned. Once patterned, the biologically-derived catalyst may precipitate a ceramic microtemplate from a solution, such that the ceramic microtemplate assumes the shape of the biologically-derived catalyst. For example, a silaffin, or a portion of a silaffin, may be patterned via controlled deposition onto an inert substrate. The silaffin may also be patterned via a method including, but not limited to, controlled phase separation from a silaffin-bearing solution, direct writing with a tip coated with the silaffin, and printing the silaffin with an ink jet printer. The patterned silaffin, or patterned portion of a silaffin, may then be exposed to a silicic acid solution so as to precipitate a silica microtemplate with the same pattern as that of the silaffin.

The chemical reaction used to partially or completely convert the biologically-derived microtemplate may be an additive reaction in which a reactant is chemically incorporated as a compound, solid solution, or mixture with the original constituents of the microtemplate. Such additive reactions are of the general type:

$$aA_bY_c + M_dX_e \Rightarrow aA_bY_c \cdot M_dX_e \qquad (1)$$

where $A_bY_c$ is a reactant, $M_dX_e$ is a constituent of the microtemplate, and $aA_bY_c \cdot M_dX_e$ is the ionically or covalently bonded new solid compound, solid solution, or solid mixture obtained from this reaction that is retained in the microcomponent; and wherein a, b, c, d, and e are any stoichiometric coefficients. For the case where $A_bY_c$, $M_dX_e$, and $A_bY_c \cdot M_dX_e$ are ionic compounds, A and M are defined as metal ions, and X and Y are defined as metalloid ions. The reactant, $A_bY_c$, involved in this additive reaction may be present as a gas, as a liquid, or as a solid or within a gas phase, within a liquid phase, or within a solid phase or a combination thereof. The reactant, $A_bY_c$, may also be deposited onto the microtemplate as a solid or liquid phase and then allowed to react, while in the solid or liquid state, with the microtemplate. An example of an additive reaction is:

$$nP_xO_y(g) + 3CaCO_3(s) \Rightarrow 3CaO \cdot nP_xO_y(s) + 3CO_2(g) \qquad (2)$$

where $P_xO_y(g)$ is a gaseous phosphorus oxide reactant species, $CaCO_3(s)$ is a solid constituent of a biologically-derived microtemplate, and $3CaO \cdot nP_xO_y(s)$ is the solid product of this additive reaction that is retained in the microcomponent.

The chemical reaction used to partially or completely convert the biologically-derived microtemplate may be a metathetic (exchange) reaction of the following type:

$$aA_bY_c + M_dX_e \Rightarrow aA_bX_{e/a} + M_dY_{ca} \qquad (3)$$

where $A_bY_c$ is a reactant, $M_dX_e$ is a constituent of the biologically-derived microtemplate, $aA_bX_{e/a}$ is an ionically or covalently bonded first solid reaction product that is a solid compound, a solid solution, or a solid mixture that is retained in the said microcomponent, and $M_dY_{ca}$ is a second reaction product; and wherein a, b, c, d, e, e/a, and ca are stoichiometric coefficients. For the case where $A_bY_c$, $M_dX_e$, $A_bX_{e/a}$, and $M_dY_{ca}$ are ionic compounds, A and M are defined as metal ions, and X and Y are defined as metalloid ions. In this metathetic reaction, the "a" moles of reactant $A_bY_c$ exchange with one mole of $M_dX_e$ to form the ironically or covalently bonded products $aA_bX_{e/a}$ and $M_dY_{ca}$. The reactant $A_bY_c$ may be a gas or a liquid or a solid or may be present within a gas mixture or a liquid solution or a liquid mixture or a solid solution or a solid compound or a solid mixture or combinations thereof. The reactant, $A_bY_c$, may be deposited onto the microtemplate as a solid or liquid phase and then allowed to react, while in the solid or liquid state, with the microtemplate. The first solid reaction product, $aA_bX_{e/a}$, may be selected from the group consisting of solid oxides, solid oxide compounds, oxide solid solutions, solid oxide mixtures, and mixtures thereof. $aA_bX_{e/a}$ may also be selected from the group consisting of lithium oxide, beryllium oxide, boron oxide, sodium oxide, magnesium oxide, aluminum oxide, potassium oxide, calcium oxide, titanium oxide, vanadium oxide, chromium oxide, manganese oxide, iron oxide, cobalt oxide, nickel oxide, copper oxide, zinc oxide, germanium oxide, rubidium oxide, strontium oxide, yttrium oxide, zirconium oxide, niobium oxide, molybdenum oxide, cadmium oxide, indium oxide, tin oxide, antimony oxide, cesium oxide, barium oxide, lanthanum oxide, hafnium oxide, tantalum oxide, tungsten oxide, lead oxide, bismuth oxide, cerium oxide, neodymium oxide, samarium oxide, europium oxide, gadolinium oxide, dysprosium oxide, holmium oxide, erbium oxide, ytterbium oxide, and mixtures thereof. The second reaction product, $M_dY_{ca}$, may be a gas or a liquid or a solid or may be present within a gas mixture or a liquid solution or a liquid mixture or a solid solution or a solid compound or a solid mixture or combinations thereof.

The chemical reaction used to partially or completely convert the biologically-derived microtemplate may be an oxidation-reduction (redox) reaction of the following type:

$$yA + aM_xO_z \Rightarrow yAO_{za/y} + axM \qquad (4)$$

where A is a reactant, $M_xO_z$ is an oxide constituent of the said biologically-derived microtemplate, $yAO_{za/y}$ is a first solid reaction product that is a solid compound, a solid solution, or a solid mixture that is retained in the shaped microcomponent, and M is a second reaction product; and wherein y, a, x, z, za/y, and ax are stoichiometric coefficients. In this redox reaction, "y" moles of the reactant A become oxidized to form "y" moles of the product oxide, $AO_{za/y}$, and "a" moles of the oxide, $M_xO_z$, are reduced to form "ax" moles of M. The first reaction product, $yAO_{za/y}$, may be selected from the group consisting of solid oxides, solid oxide compounds, oxide solid solutions, solid oxide mixtures, and mixtures thereof. $yAO_{za/y}$ may also be selected from the group consisting of lithium oxide, beryllium oxide, magnesium oxide, aluminum oxide, calcium oxide, titanium oxide, strontium oxide, yttrium oxide, zirconium oxide, antimony oxide, barium oxide, lanthanum oxide, hafnium oxide, cerium oxide, neodymium oxide, praseodymium oxide, samarium oxide, europium oxide, gadolinium oxide, dysprosium oxide, holmium oxide, erbium oxide, thulium oxide, lutetium oxide, ytterbium oxide, and mixtures thereof. The reactant, A, may be a gas or a liquid or a solid or may be present within a gas mixture or a liquid solution or a liquid mixture or a solid solution or a solid compound or a solid mixture or combinations thereof. The reactant, A, may be deposited onto the microtemplate as a solid or liquid phase and then allowed to react, while in the solid or liquid state, with the microtemplate. The second reaction product, M, may be selected from the group consisting of a pure solid, a solid alloy, a solid compound, a solid mixture, a pure liquid, a liquid alloy, a pure gas, a gas mixture, and mixtures thereof. Hence, if the biologically-derived microtemplate is the silica frustule of a diatom, then a redox reaction may be used to exchange the silicon in silicon oxide (silica) with a displacing reactant species, so as to convert the silicon oxide into a different metal oxide compound. An example of such a redox reaction is:

$$2Mg(g) + SiO_2(s) \Rightarrow 2MgO(s) + Si(s) \qquad (5)$$

where $Mg(g)$ is a gaseous displacing reactant species, $SiO_2(s)$ (silica) is a solid oxide constituent of a microtemplate, and MgO(s) is the solid oxide product of this redox reaction that is retained in the microcomponent. In this example, Mg(g) is the displacing reactant species that is oxidized to form MgO and $SiO_2$(s) is reduced to form Si(s). In this example, the displacing reactant species may be any reactant species adapted to reduce the silicon oxide into silicon. For instance, the said displacing reactant species may be selected from the group consisting of alkaline earth elements, such as beryllium, magnesium, calcium, strontium, barium, and mixtures thereof. The said displacing reactant species may also be selected from the group consisting of alkali elements, such as hydrogen, lithium, and mixtures thereof. The said displacing reactant species may also be selected from the group consisting of aluminum, titanium, zirconium, hafnium, yttrium, lanthanum, cerium, praesodymium, neodymium, samarium, europium, gadolinium, terbium, dysprosium, holmium, erbium, thulium, ytterbium, lutetium, thorium, uranium, and mixtures thereof.

The shaped microcomponent may define a space wherein the space is provided with at least one additional non-native substance. The at least one additional non-native substance may be a pharmaceutically active substance.

The shaped microcomponent may also possess pores with a controlled size and/or shape distribution for filtration or separation of components within fluid streams. Such fluid streams may be gas streams or liquid streams, or mixtures of gas and liquid streams. The components within the fluid stream may be solid particles entrained within the fluid stream, or a liquid species dissolved in the fluid stream, or a gas species dissolved within the fluid stream, or some combination thereof. For example, the component within the fluid stream may be a protein or blood cell. The component within the fluid stream may also be a virus, bacteria, or other biological agent.

The shaped microcomponent may also possess a shape and/or chemistry that enhances the mixing of two or more fluids that pass by or through the microcomponent.

The shaped microcomponent may be a powder with a controlled average shape and/or a controlled shape distribution, and/or a controlled average size, and/or a controlled size distribution. The shaped microcomponent may be a filler material with a controlled average shape, and/or a controlled shape distribution, and/or a controlled average size, and/or a controlled size distribution. The shaped microcomponent may be a reinforcement material with a controlled average shape, and/or a controlled shape distribution, and/or a controlled average size, and/or a controlled size distribution.

The shaped microcomponent may possess a shape selected from the group consisting of a solid microcylinder, a microtube, a solid microbar, a hollow microbar, a solid microsphere, a hollow microsphere, a solid microdisk, a hollow microdisk, a microwheel, a microgear, a microrotor, a microplate, a microtetrahedron, a microwedge, a microtetrakaidecahedron, a microspring, a microspiral, a microlever, a microcantilever, a solid microcone, a microfunnel, a microhoneycomb, a micromesh, a solid microcube, a hollow microcube, a solid microfiber, a hollow microfiber, and combinations thereof The shaped microcomponent may be used in a device selected from the group consisting of a micro-pump, a micro-valve, a micro-funnel, a micro-nozzle, a micro-reactor, a micro-bearing, a micro-pulley, a micro-turbine engine, a micro-rocket, a micro-piston engine, a micro-motor, a micro-actuator, a micro-switch, a micro-transducer, a micro-hinge, a micro-cantilever, a micro-relay, a micro-die, a micro-sensor, a micro-catalyst, a micro-syringe, a micro-needle, a micro-capsule, a micro-sieve, a micro-filter, a micro-membrane, a micro-separator, a micro-mirror, a micro-lens, a micro-prism, a micro-diffraction grating, a micro-refraction grating, a micro-antenna, a micro-magnet, a micro-tag, a micro-fiber, a micro-light pipe, a micro-mixer, a micro-heat exchanger, a micro-insulator, a micro-substrate, a micro-filler, and combinations thereof.

The shaped microcomponent may possess a functional property selected from the group consisting of an optical property, a magnetic property, an electrical property, a chemical property, a biological property, a thermal property, a mechanical property, and combinations thereof.

The present invention also includes a method for the production of a shaped microcomponent comprising the steps of obtaining at least one biologically-derived microtemplate having an original chemical composition, and an original dimensional feature; and subjecting the at least one biologically-derived microtemplate to a first chemical reaction, so as to partially or completely convert the at least one biologically-derived microtemplate into an intermediate microcomponent having a second chemical composition different than the original chemical composition; and then subjecting the intermediate microcomponent to a second chemical reaction so as to partially or completely convert the intermediate microcomponent into the shaped microcomponent having a chemical composition different than the original chemical composition and different than the second chemical composition and having substantially the same dimensional feature as the original dimensional feature.

The present invention is also to a method for the production of a shaped microcomponent comprising the steps of: obtaining at least one biologically-derived microtemplate having an original chemical composition, and an original dimensional feature; and subjecting said at least one biologically-derived microtemplate to a first chemical reaction, so as to partially or completely convert said at least one biologically-derived microtemplate into an intermediate microcomponent having a second chemical composition different than said original chemical composition; and then subjecting said intermediate microcomponent to at least one subsequent chemical reaction so as to partially or completely convert the said intermediate microcomponent into said shaped microcomponent having a chemical composition different than said original chemical composition and different than said second chemical composition and having substantially the same dimensional feature as said original dimensional feature.

The present invention is also to a method for the production of shaped, biologically-derived microcomponents comprising the steps of: obtaining at least one diatom frustule having an original chemical composition and an original dimensional feature, wherein said original chemical composition comprises silica; and subjecting said at least one diatom frustule to an oxidation-reduction reaction, so as to partially or completely convert the diatom frustule into a microcomponent having a chemical composition different than said original chemical composition and having substantially the same dimensional features as the said original diatom frustule.

Additionally, the present invention is to a method for the production of a shaped microcomponent comprising the steps of: obtaining at least one diatom frustule having an original chemical composition, and an original dimensional feature; wherein the original chemical composition comprises silica; subjecting the at least one diatom frustule to a first chemical reaction so as to partially or completely convert the at least one diatom frustule into an intermediate microcomponent having a second chemical composition different than the original chemical composition; and then subjecting the intermediate microcomponent to a second chemical reaction so as to partially or completely convert the intermediate microcomponent into a shaped microcomponent having a chemical composition different than the original chemical composition and different than the second chemical composition and having substantially the same dimensional feature as the original dimensional feature.

Additionally, the present invention is to a method for the production of a shaped microcomponent comprising the steps of: obtaining at least one diatom frustule having an original chemical composition, and an original dimensional feature; wherein the original chemical composition comprises silica; subjecting the at least one diatom frustule to a first chemical reaction so as to partially or completely convert the at least one diatom frustule into an intermediate microcomponent having a second chemical composition different than the original chemical composition; and then subjecting the intermediate microcomponent to at least one subsequent chemical reaction so as to partially or completely convert the intermediate microcomponent into a shaped microcomponent having a chemical composition different than the original chemical composition and different than the second chemical composition and having substantially the same dimensional feature as the original dimensional feature.

The microcomponent may be a chemically altered template. The shaped microcomponent may be derived from an article having an original chemical composition and an original shape and/or an original surface feature, the original chemical composition having been converted to an altered composition while retaining the original shape. The shaped microtemplate may be a diatom frustule. The diatom frustule may comprise silica. The chemically altered diatom frustule may have been chemically converted to partially or substantially replace said silica.

Among the reactions that may be used to convert silica-based microtemplates (e.g., diatom frustules) Into other oxides or oxide/metal composites are solid/fluid displacement (oxidation-reduction) reactions of the following type:

$$SiO_2(s) + 2/y\, M(g) \Rightarrow 2/y\, MO_y(s) + (Si) \qquad (6)$$

$$SiO_2(s) + 2/y\, M(l) \Rightarrow 2/y\, MO_y(s) + (Si) \qquad (7)$$

where (Si) refers to silicon present as a pure solid, liquid, or gas or to silicon dissolved in a solid, liquid, or gas solution. For example, prior work has shown that silica ($SiO_2(s)$) may be converted into $Al_2O_3/Al$—Si composites that retain the shape/dimensions within 1% by the following net reaction:

$$3SiO_2(s) + 4Al(l) \Rightarrow 2Al_2O_3(s) + (Si) \qquad (8)$$

where (Si) refers to an Al—Si alloy. Exposing silica microtemplates (e.g., diatom frustules of genetically-tailored shapes) to Al-rich liquid alloys may produce such composites. The silica (e.g., in the diatom frustule walls) may be converted into a dense mixture of $Al_2O_3(s)$ and Al—Si alloy with little less than or eaual to 1%) change in dimensions or shape. That is, although 2 moles of $Al_2O_3(s)$ possess a smaller volume than 3 moles of $SiO_2(s)$, the difference in these volumes is taken up by the liquid Al—Si (and, hence, solid Al—Si upon solidification of this liquid). After such reaction, the excess solidified Al—Si within the transformed silica microtemplate may be removed by selective etching/dissolution to yield an $Al_2O_3(s)$ body that retains the shape and/or surface features of the starting silica microtemplate.

Displacement (oxidation-reduction) reactions of the following type may also be used to convert silica-based microtemplates into other oxides or oxide/metal composites:

$$2Ca(l) + SiO_2(s) \Rightarrow 2CaO(s) + (Si) \qquad (9)$$

$$2Sr(l) + SiO_2(s) \Rightarrow 2SrO(s) + (Si) \qquad (10)$$

$$2Ba(l) + SiO_2(s) \Rightarrow 2BaO(s) + (Si) \qquad (11)$$

where (Si) refers to silicon present as a pure solid, liquid, or gas or to silicon dissolved in a solid, liquid, or gas solution. For these reactions, the oxide produced has a larger volume than the oxide consumed (e.g., 2 moles of CaO(s) have a larger volume than 1 mole of $SiO_2(s)$). In these cases, although the overall silica microtemplate shape may be retained upon reaction, some surface features may be controllably altered (e.g., some of the fine pores of the silica microtemplate may be filled in with new ceramic). Alternately, depending on the reaction conditions, the silica microtemplate may expand upon reaction to yield a larger component with the same shape and with surface features of the same size. If the (Si) product of reactions (9)–(1 1) is present as a solid phase, then such silicon may be removed from the converted microcomponent (e.g., by selective dissolution), so as to yield microcomponents comprised of only oxides. CaO-bearing bodies may be particularly attractive for biomedical applications, given the biocompatibility of CaO-bearing compositions in the human body (i.e., CaO-bearing compositions may dissolve in blood and be used to enhance natural bone growth).

In addition to forming single component oxides, reactions may be chosen that yield multicomponent oxides. For example, $$Mg_1Al_2(l) + 2SiO_2(s) \Rightarrow MgAl_2O_4(s) + 2(Si) \qquad (12)$$

where (Si) refers to silicon present as a pure solid, liquid, or gas or to silicon dissolved in a solid, liquid, or gas solution. Spinel, $MgAl_2O_4$, is a relatively high melting, refractory oxide with good resistance to chemical attack by basic or acidic oxide liquids or by reactive gases (e.g., sodium vapor in lamps for optical applications).

Reactions may also be chosen that yield multicomponent metal products, such as silicides:

$$X_{4/y}Mo(l) + 2SiO_2(s) \Rightarrow 4/y\, XO_y(s) + MoSi_2(s) \qquad (13)$$

where X refers to an element capable of undergoing a displacement reaction with $SiO_2(s)$. $MoSi_2(s)$ is a relatively high melting and oxidation-resistant intermetallic compound.

Oxidation-reduction reactions or metathetic reactions with silica microtemplates may also involve gas-phase reactants. Two examples of gas/silica oxidation reduction reactions are shown below:

$$2Mg(g) + SiO_2(s) \Rightarrow 2MgO(s) + (Si) \qquad (14)$$

$$2Ca(g) + SiO_2(s) \Rightarrow 2CaO(s) + (Si) \qquad (15)$$

where (Si) refers to silicon present as a pure solid, liquid, or gas or to silicon dissolved in a solid, liquid, or gas solution. By using such gas/solid reactions to transform $SiO_2(s)$, excess solid metallic reactant (e.g., excess Mg or Ca) adhering to the converted body may be avoided, unlike for the case of liquid/solid oxidation-reduction reactions. For oxidation-reduction reactions involving a liquid metallic reactant, excess solidified metallic reactant adhering to and surrounding the converted oxide component must be removed upon cooling in order to extract the microcomponent. This removal of excess metal is an additional time-consuming step that may be avoided by using gas/solid oxidation-reduction reactions. Hence, such gas/solid oxidation-reduction reactions have an inherent advantage over liquid/solid oxidation-reduction reactions and are preferred for the present invention.

Several thermodynamically-favored gas/silica reactions (oxidation-reduction and metathetic reactions) are shown in Table 1 below.

If the (Si) product of reactions (14) and (15) is present as a solid phase (either pure solid silicon or a silicon-bearing solid), then such silicon may be removed from the converted microcomponent (e.g., by selective dissolution), so as to yield microcomponents comprised of only oxides. Alternately, a condensed (Si) product phase may be oxidized by reaction with gaseous oxygen to convert the silicon back into $SiO_2(s)$. Subsequent oxide-oxide reactions may then be used to produce microcomponents comprised of multioxide compounds. For example, reoxidation of a solid (Si) product in reaction (14) to $SiO_2(s)$ followed by the following oxide-oxide reaction may yield a microcomponent comprised of forsterite, $Mg_2SiO_4(s)$:

$$2MgO(s) + SiO_2(s) \Rightarrow Mg_2SiO_4(s) \tag{16}$$

Oxidation-reduction reactions may also be used to partially consume the silica in the microtemplates, so that subsequent oxide-oxide reactions may be used to produce microcomponents comprised of multioxide compounds. Consider, for example, the following reactions:

$$2Mg(g) + 2SiO_2(s) \Rightarrow 2MgO(s) + SiO_2(s) + (Si) \tag{17}$$

$$3Ca(g) + 5/2SiO_2(s) \Rightarrow 3CaO(s) + SiO_2(s) + 3/2(Si) \tag{18}$$

where (Si) refers to silicon present as a pure solid, liquid, or gas or to silicon dissolved in a solid, liquid, or gas solution. In these reactions, the silica is only partially consumed (i.e., only 1 of 2 moles of silica is reduced by the Mg(g) or Ca(g)). Further heat treatment of the oxide products of reactions (17) and (18) in the

TABLE 1

Examples of other thermodynamically-favored gas/silica reactions.

| Gas/Silica Reaction[a] | Reaction Temperature (° C.) | Pressure of Reactant Gas[b] (torr) | Free Energy of Reaction[c] (kJ/mole) |
|---|---|---|---|
| 1) $4/3AlF_3(g) + SiO_2(s)$ $\Rightarrow 2/3Al_2O_3(s) + SiF_4(g)$ | 1150 | 101 | −78.2 |
| 2) $2Ca(g) + SiO_2(s)$ $\Rightarrow 2CaO(s) + \{Si\}$ | 1200 | 100 | −354.0 |
| 3) $4/3FeF_3(g) + SiO_2(s)$ $\Rightarrow 2/3Fe_2O_3(s) + SiF_4(g)$ | 800 | 140 | −55.7 |
| 4) $4Li(g) + SiO_2(s)$ $\Rightarrow 2Li_2O(s) + \{Si\}$ | 1100 | 106 | −246.0 |
| 5) $4/5NbF_5(g) + SiO_2(s)$ $\Rightarrow 2/5Nb_2O_5(s) + SiF_4(g)$ | 900 | [d] | −74.1 |
| 6) $2Sr(g) + SiO_2(s)$ $\Rightarrow 2SrO(s) + \{Si\}$ | 1150 | 102 | −275.6 |
| 7) $4/5TaF_5(g) + SiO_2(s)$ $\Rightarrow 2/5Ta_2O_5(s) + SiF_4(g)$ | 900 | [d] | −80.4 |
| 8) $TiF_4(g) + SiO_2(s)$ $\Rightarrow TiO_2(s) + SiF_4(g)$ | 900 | [d] | −68.9 |

TABLE 1-continued

Examples of other thermodynamically-favored gas/silica reactions.

| Gas/Silica Reaction[a] | Reaction Temperature (° C.) | Pressure of Reactant Gas[b] (torr) | Free Energy of Reaction[c] (kJ/mole) |
|---|---|---|---|
| 9) $ZrF_4(g) + SiO_2(s)$ $\Rightarrow ZrO_2(s) + SiF_4(g)$ | 900 | 667 | −94.0 |

[a]{Si} refers to silicon dissolved in a molten metallic liquid (e.g., a binary Ca-Si solution).
[b]Equilibrium partial pressure of the gaseous reactant over the pure condensed phase of the same composition at the indicated reaction temperature (e.g., the partial pressure of Ca(g) over Ca(l) at 1200° C. is 100 torr), as calculated from thermodynamic data.
[c]The Gibbs free energy of reaction per mole of silica consumed, $\Delta G_{rxn}$, was calculated using pure component reference states for the gases, solid oxides, and {Si}.
[d]The reaction temperature is well in excess of the boiling or sublimation point of the reactant species (the boiling point of $NbF_5(l)$ is 236° C.; the sublimation point of $TiF_4(s)$ is 285° C.; the boiling point of $TaF_5(l)$ is 228° C.).

absence of gaseous Mg or Ca may result in the formation of the refractory compounds, $Mg_2SiO_4$ and $Ca_3SiO_5$, by the following oxide-oxide reactions:

$$2MgO(s) + SiO_2(s) \Rightarrow Mg_2SiO_4(s) \tag{19}$$

$$3CaO(s) + SiO_2(s) \Rightarrow Ca_3SiO_5(s) \tag{20}$$

Oxidation-reduction reactions with silica microtemplates may also be used to produce microcomponents comprised of oxide/intermetallic composites, such as shown below:

$$2Mg(g) + SiO_2(s) \Rightarrow 2MgO(s) + Mg_2Si(s) \tag{21}$$

$$2Ca(g) + SiO_2(s) \Rightarrow 2CaO(s) + Ca_2Si(s) \tag{22}$$

A series of fluid/solid reactions may also be used to convert silica microtemplates (e.g., diatom frustules) into multicomponent ceramics. For example, silica microtemplates may first be converted into MgO or CaO by one of the following oxidation-reduction reactions:

$$2Mg(l) + SiO_2(s) \Rightarrow 2MgO(s) + (Si) \tag{23}$$

$$2Mg(g)) + SiO_2(s) \Rightarrow 2MgO(s) + (Si) \tag{24}$$

$$2Ca(l) + SiO_2(s) \Rightarrow 2CaO(s) + (Si) \tag{25}$$

$$2Ca(g)) + SiO_2(s) \Rightarrow 2CaO(s) + (Si) \tag{26}$$

where (Si) refers to silicon present as a pure solid, liquid, or gas or to silicon dissolved in a solid, liquid, or gas solution. After selective removal of the (Si) product (e.g., by selective dissolution), the resulting, shaped MgO or CaO microbodies may then undergo further reaction(s) to produce shaped microbodies comprised of MgO-bearing or CaO-bearing compounds. For example, the following types of additive reactions may be used to convert the MgO or CaO into compounds containing these oxides:

$$MgO(s) + 1/3W_3O_9(g) \Rightarrow MgWO_4(s) \tag{27}$$

$$MgO(s) + 2CrO_3(g) \Rightarrow MgCr_2O_4(s) + 3/2O_2(g) \tag{28}$$

$$mCaO(s) + nP_xO_y(g) \Rightarrow mCaO \cdot nP_xO_y(s) \tag{29}$$

$$mCaO(s) + nP_xO_y(g) + pH_2O(g) \Rightarrow mCaO \cdot nP_xO_y \cdot pH_2O \tag{30}$$

where $P_xO_y(g)$ refers to a gaseous P-O-bearing species, $mCaO \cdot nP_xO_y(s)$ refers to a calcium phosphate compound (e.g., $Ca_2P_2O_7$, $Ca_3P_2O_8$), and $mCaO \cdot nP_xO_y \cdot pH_2O(s)$ refers to hydrated calcium phosphate compounds (e.g., calcium hydroxyapatite, $10CaO \cdot 6P_xO_y \cdot 2H_2O$). Calcium phosphate microcomponents may be particularly attractive for biomedical applications. For example, because calcium hydroxyapatite is the major mineral in human teeth and bones, the body does not reject this compound. Hence calcium hydroxyapatite microcomponents derived from silica microtemplates would be biocompatible. Such biocompatible microcomponents would be particularly attractive for biomedical applications (e.g., bioresorbable microcapsules for targeted drug or radiation delivery). Magnesium tungstate, $MgWO_4$, is a luminescent material that can be attractive for lighting or other optical applications. Magnesium chromite, $MgCr_2O_4$, is a refractory ceramic that is resistant to chemical attach by silicate slags and, hence, is attractive as a corrosion-resistant lining material. Magnesium chromite is also the major component in commercial water vapor sensors (e.g., titania-doped magnesium chromite).

The present invention is also to a method for the production of shaped, biologically-derived microcomponents comprising the steps of: a) obtaining at least one naturally-occurring microtemplate having an original chemical composition and an original dimensional feature, wherein said original chemical composition comprises calcium carbonate; and b) subjecting said at least one naturally-occurring microtemplate to a chemical reaction, so as to partially or completely convert the microtemplate into a microcomponent having a chemical composition different than said original chemical composition and having substantially the same dimensional features as the said original microtemplate.

As mentioned above, several naturally-occurring microtemplates are comprised of calcium carbonate, including, but not limited to: the spicules of sponges and the shells of mollusks and coccolithophores.

The chemical compositions of calcium carbonate microtemplates may be changed by additive reactions. Such additive reactions may involve gas-phase reactants, as shown below (and mentioned above):

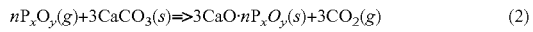 (2)

Alternately, condensed phase reactants may be deposited onto the calcium carbonate microtemplate by a vapor phase technique (including, but not limited to, sputtering, laser ablation, evaporation, and chemical vapor deposition) or a liquid phase technique (including, but not limited to, melt infiltration, solution infiltration, slurry infiltration). After deposition of the reactants, the calcium carbonate may then undergo an additive reaction with the reactant. Examples of additive reactions between condensed phase reactants and calcium carbonate include, but are not limited to:

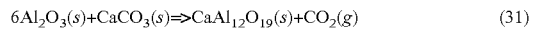 (31)

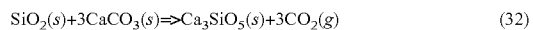 (32)

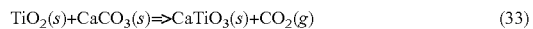 (33)

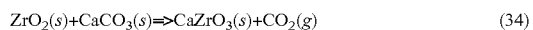 (34)

Metallic precursors to oxide reactants may also deposited onto the calcium carbonate microtemplate by a vapor phase technique or a liquid phase technique, and then oxidized to form an oxide reactant. The oxide reactant may then undergo reaction with the calcium carbonate to form a new compound, solid solution, or mixture. Examples of metallic precursors that may be deposited, oxidized, and then reacted with calcium carbonate include, but are not limited to phosphorus, aluminum, silicon, titanium, and zirconium (i.e., oxidation of these deposited elements may be followed by reactions with calcium carbonate as per reactions (2) and (31)–(34)).

Additive reactions of the type (2) and (31)–(34) may also be used to convert silica microtemplates into silicate compounds. Examples of such additive reactions include, but are not limited to:

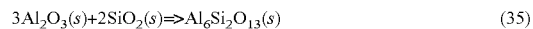 (35)

 (36)

 (37)

 (38)

Metallic precursors to oxide reactants may also deposited onto the silica microtemplate by a vapor phase technique or a liquid phase technique, and then oxidized to form an oxide reactant. The oxide reactant may then undergo reaction with the silica to form a new compound, solid solution, or mixture. Examples of metallic precursors that may be deposited, oxidized, and then reacted with silica include, but are not limited to aluminum, calcium, magnesium, and zirconium (i.e., oxidation of these deposited elements may be followed by reactions with silica as per reactions (35)–(38)).

The present invention is focused on a revolutionary, low-cost (highly-scaleable) approach for the mass production of Genetically-Engineered Materials (GEMs): the biological reproduction of naturally-occurring and/or biocatalyzed or genetically-tailored three-dimensional microtemplates (e.g., diatom frustules, mollusk shells), followed by reactive conversion of such templates into microcomponents with new, more desired compositions with a retention of the shapes and/or surface features of the microtemplates.

DETAILED DESCRIPTION OF THE PREFERRED EMBODIMENT(S)

EXAMPLE 1

Figure 1:
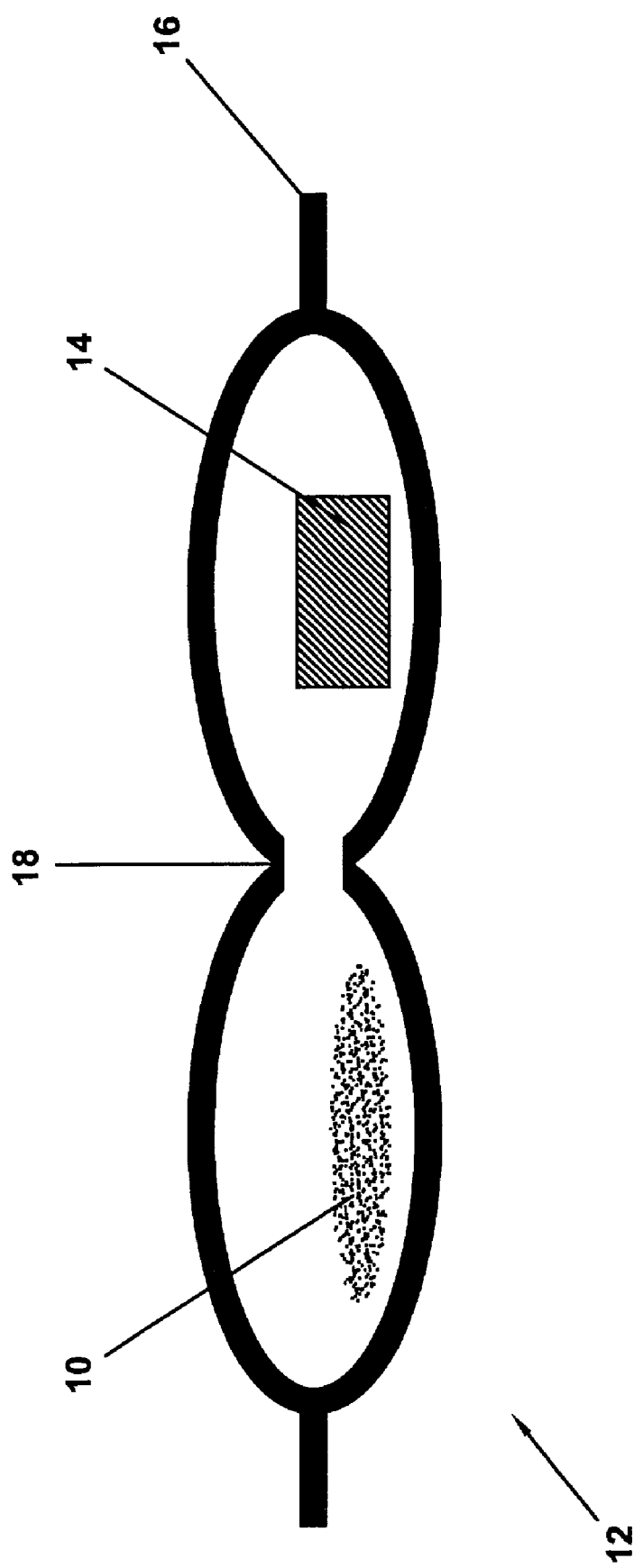
FIG. 1 is a schematic of the assembly used to react diatomaceous earth powder with gaseous magnesium.
Figure 2A:
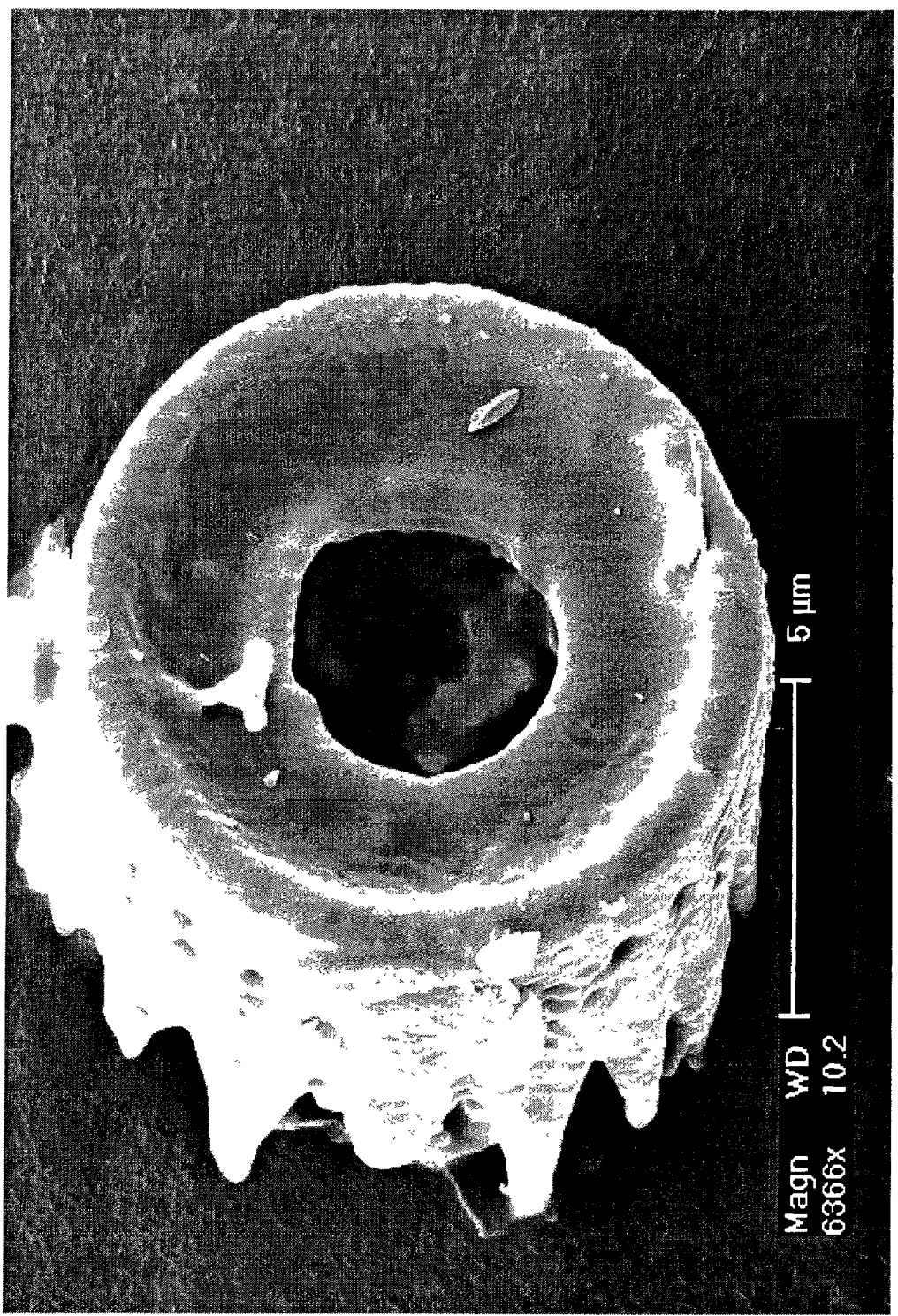
FIG. 2A is a secondary electron image of the frustule of a naturally-occurring Aulacoseira diatom in accordance with one embodiment of the present invention.
Figure 2B:
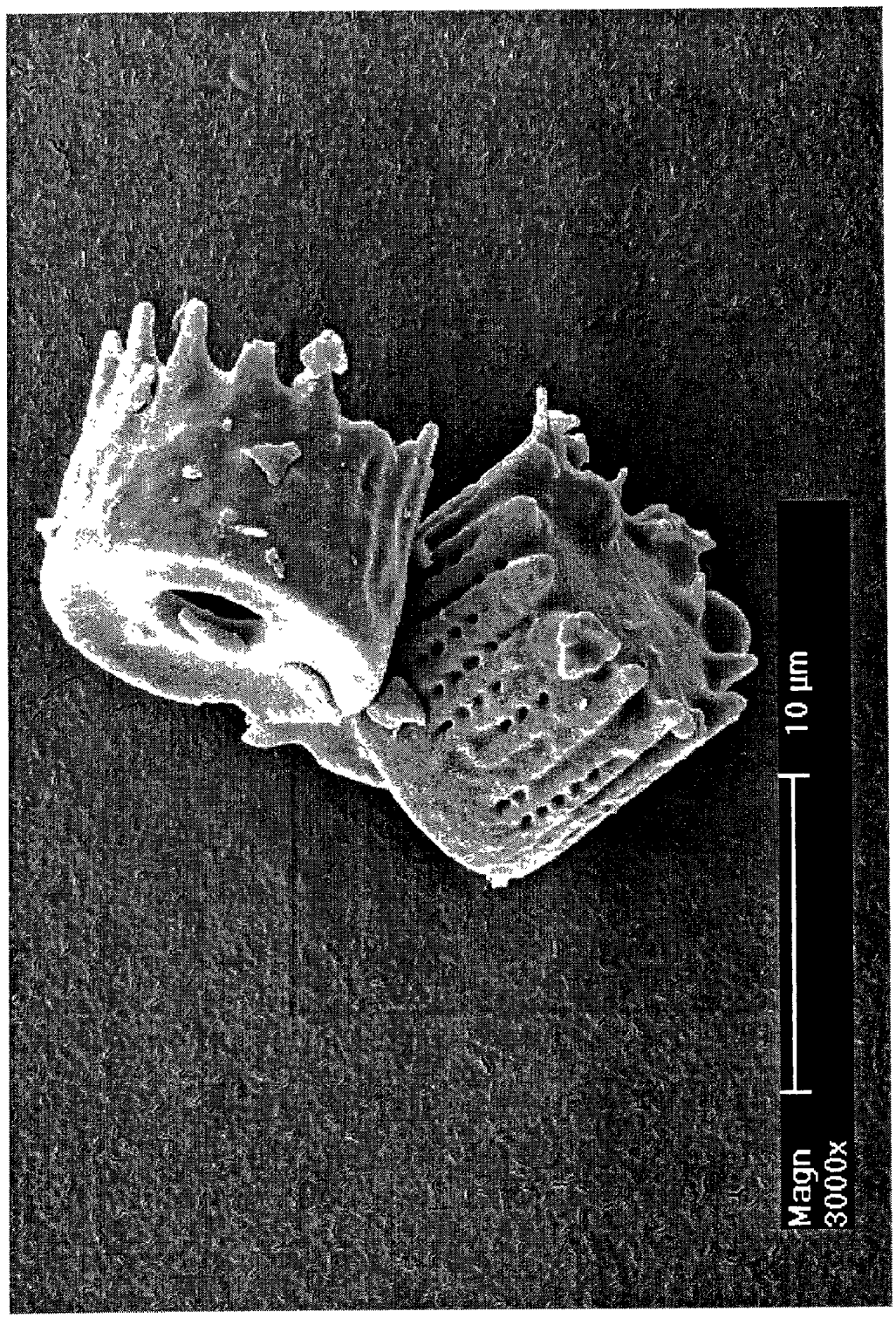
FIG. 2B is a secondary electron image of the frustule of a naturally-occurring Aulacoseira diatom in accordance with one embodiment of the present invention.
Figure 2C:
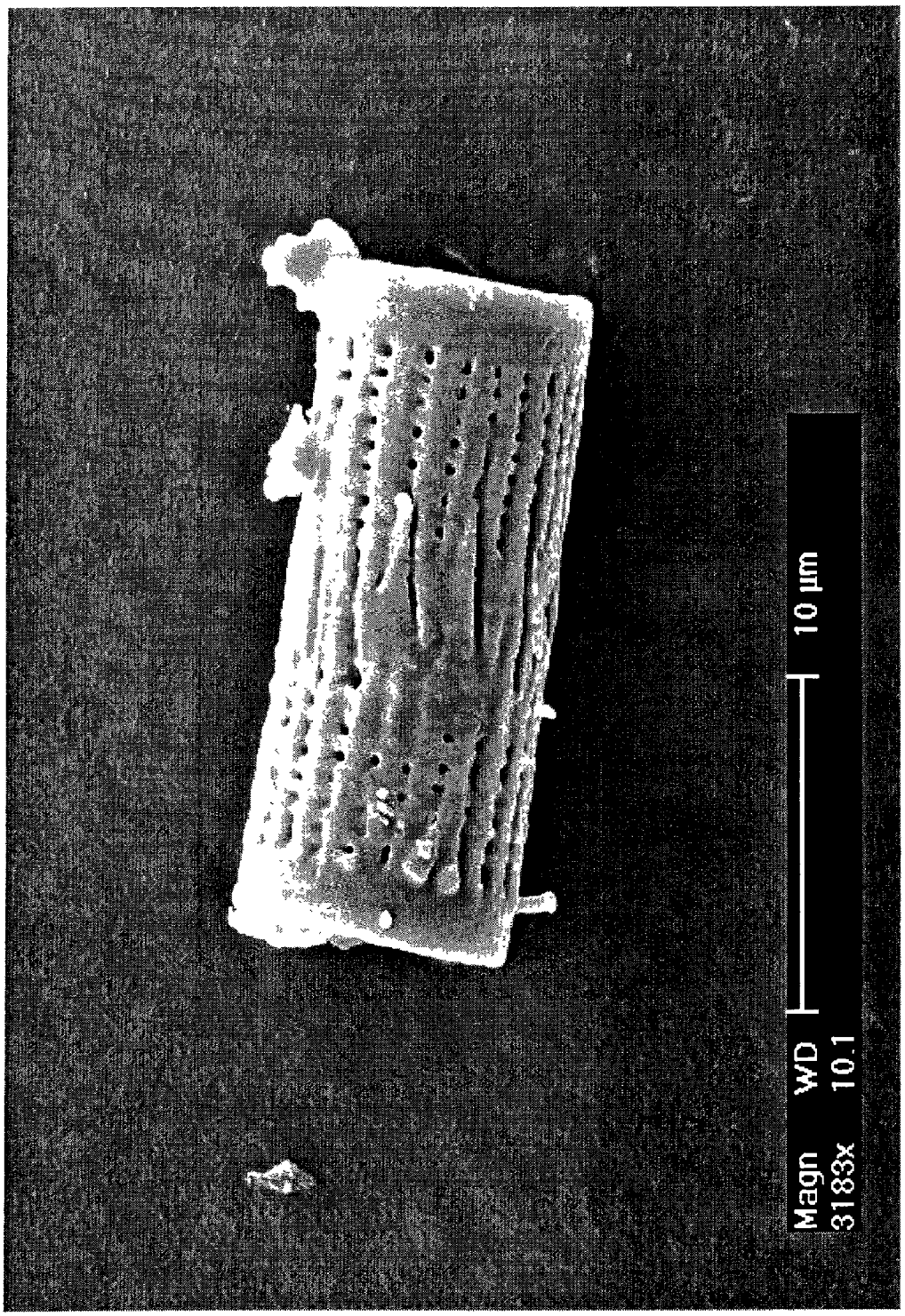
FIG. 2C is a secondary electron image of the frustule of a naturally-occurring Aulacoseira diatom in accordance with one embodiment of the present invention.

Conversion of a $SiO_2$-based Diatom Frustule into a MgO Microcomponent with Preservation of the Starting Frustule Shape Diatomaceous earth was obtained from a local vendor. Examination of this batch of diatomaceous earth with scanning electron microscopy revealed that the predominant diatom species was Aulacoseira (see FIG. 2 below). As seen in FIG. 2A–2C, the frustule of the Aulacoseira diatom possessed a cylindrical shape, with fine pores running in rows along the walls of the cylinder. As seen in FIGS. 2A and 2B, one end of the cylinder was open and the other end was closed (note: the image in FIG. 2C reveals two Aulacoseira frustule cylinders connected together end-to-end). Prior to conducting the reactions discussed below, these diatoms were placed in a ceramic crucible and then heated to 60000 for a total of 8 hours in air, in order to burn away any residual organic material. With regard to FIG. 1, the Aulacoseira frustules 10 were then sealed inside a steel tube 12 along with some solid pieces of pure magnesium 14. Such sealing was conducted to allow for the development of a significant magnesium vapor pressure within the chamber upon heating (note: a steel tube was used, as the major constituent in steel, iron, is chemically inert with respect to magnesium and silica). The sealing was conducted by crimping the ends of the tube and then welding the ends shut 16. The diatomaceous earth and magnesium were physically separated into two chambers within the tube by midsection crimp 18.

By crimping the midsection of the steel tube so as to form a narrow orifice, two chambers were created. After sealing the tube, the assembly was heated in an inert atmosphere (Ar) tube furnace for 4 hours at 900° C. During heating to 900° C., the solid magnesium melted (the melting point of pure magnesium is about 650° C.). At 900° C., a significant magnesium vapor pressure was generated within the steel tube (the vapor pressure of Mg(g) over Mg(s) at 900° C. at a total pressure of 1 atm is about 120 torr, or about 0.16 atm). The Mg(g) migrated to the chamber containing the diatom frustules and underwent a net displacement reaction of the following type with the $SiO_2$ in the Aulacoseira diatom frustules:

$$2Mg(g)+SiO_2(s) \Rightarrow 2MgO(s)+(Si) \qquad (1)$$

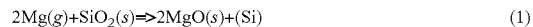

where (Si) refers to silicon dissolved within a Mg-Si liquid. After this heat treatment, the steel tube was cut open and the reacted diatomaceous earth powder was removed.

Secondary electron images of Aulacoseira frustules prior to reaction are shown in FIGS. 2A–C. These images reveal that the cylinder-shaped Aulacoseira frustules contained small pores running in rows along the cylinder wall. As shown in FIGS. 2A and B, one end of each frustule contained a larger hole, whereas the other end was closed. Secondary electron images obtained after reaction with Mg(g) for 4 hours at 900° C. in the manner discussed above are shown in FIGS. 3A and 3B. Although the reacted frustules in FIGS. 3A or 3B appear more granular than those in FIGS. 2A, 2B or 2C (due to the reaction that occurred with Mg(g)), comparison of the images in FIGS. 2A, 2B or 2C and 3A or 3B reveals that the general shape and features of the diatom frustule were retained upon reaction.

Figure 3A:
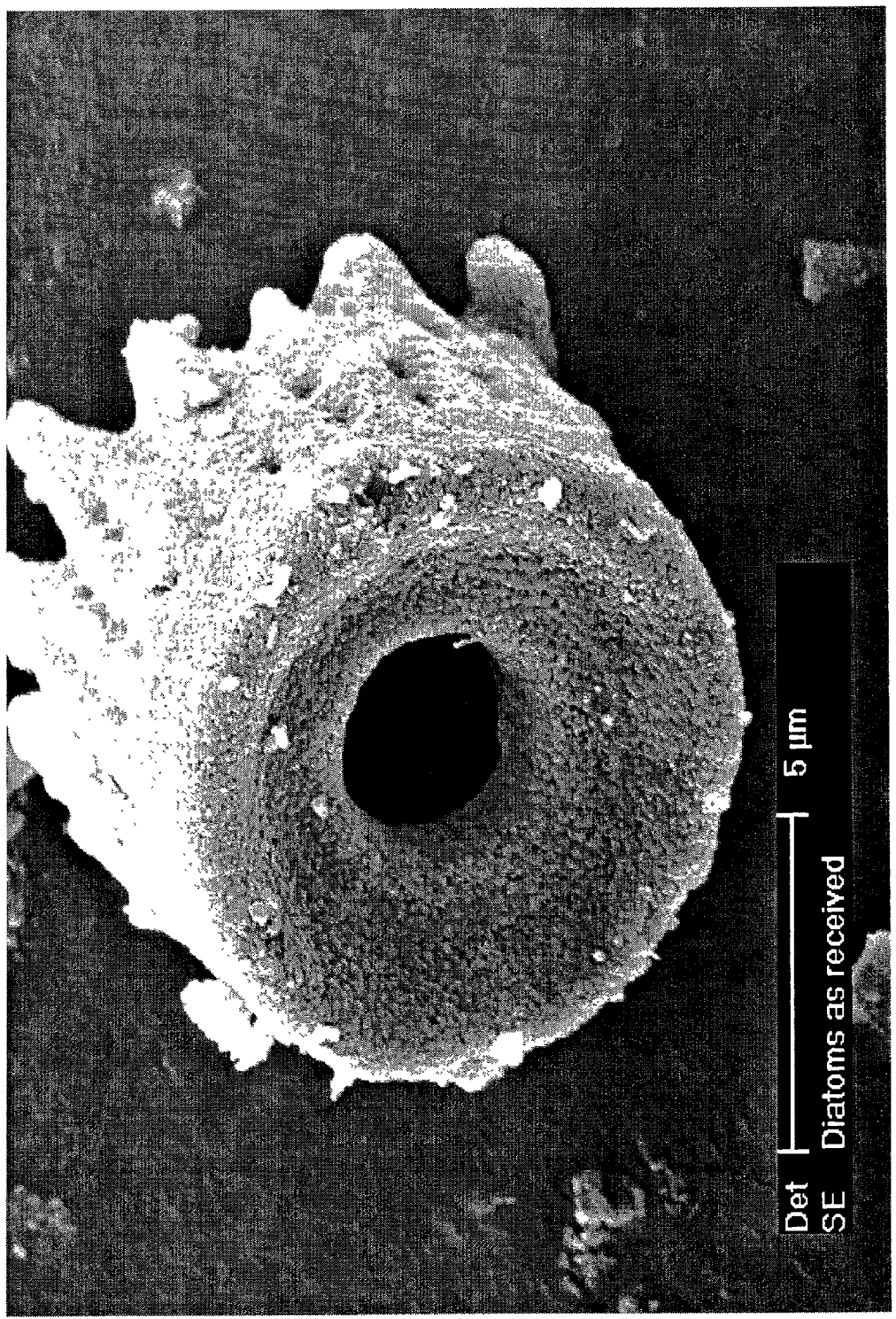
FIG. 3A is a secondary electron image of the frustule of a naturally-occurring Aulacoseira diatom after reaction with gaseous magnesium for 4 hours at 900° C. in accordance with one embodiment of the present invention.
Figure 3B:
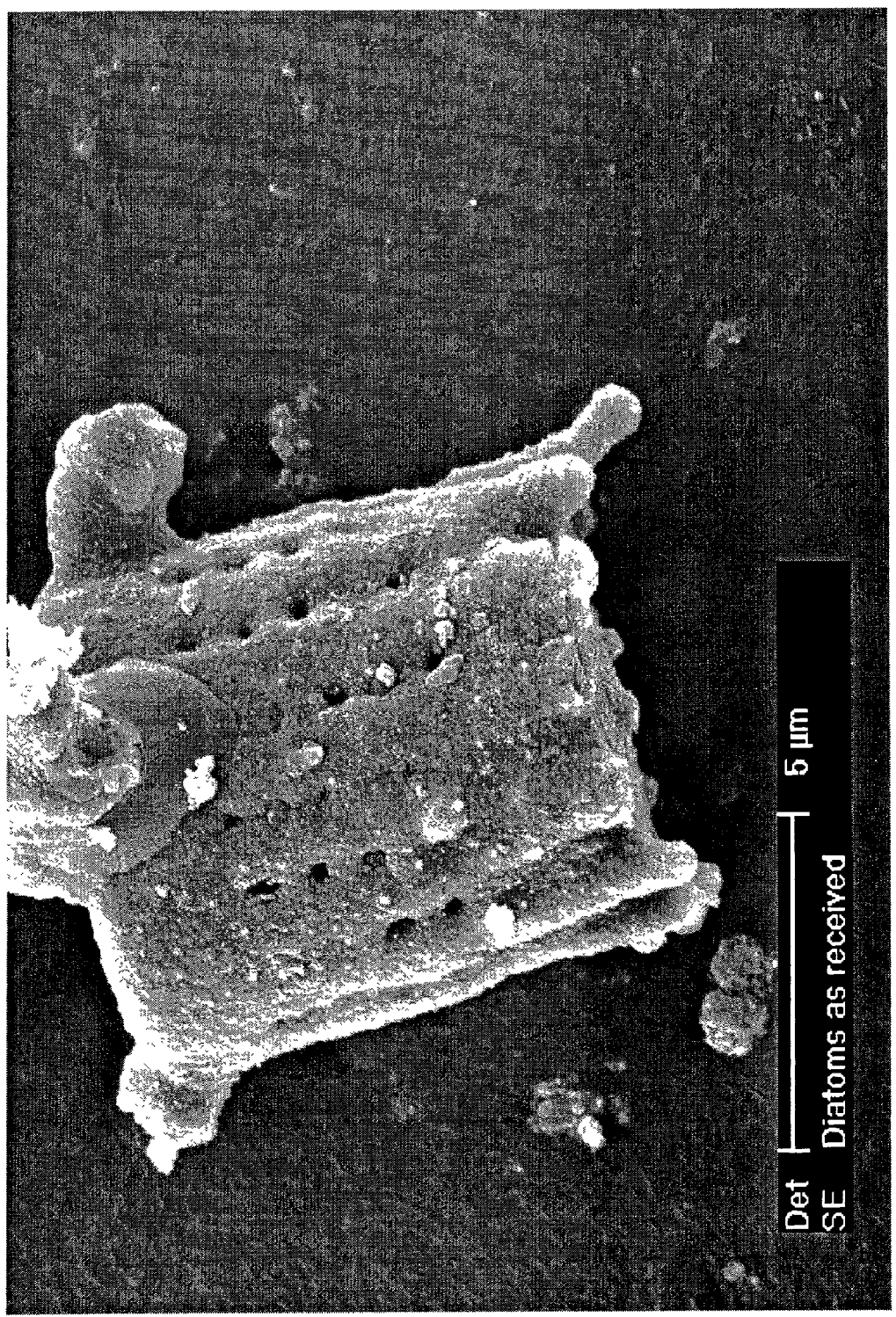
FIG. 3B is a secondary electron image of the frustule of a naturally-occurring Aulacoseira diatom after reaction with gaseous magnesium for 4 hours at 900° C. in accordance with one embodiment of the present invention.
Figure 4A:
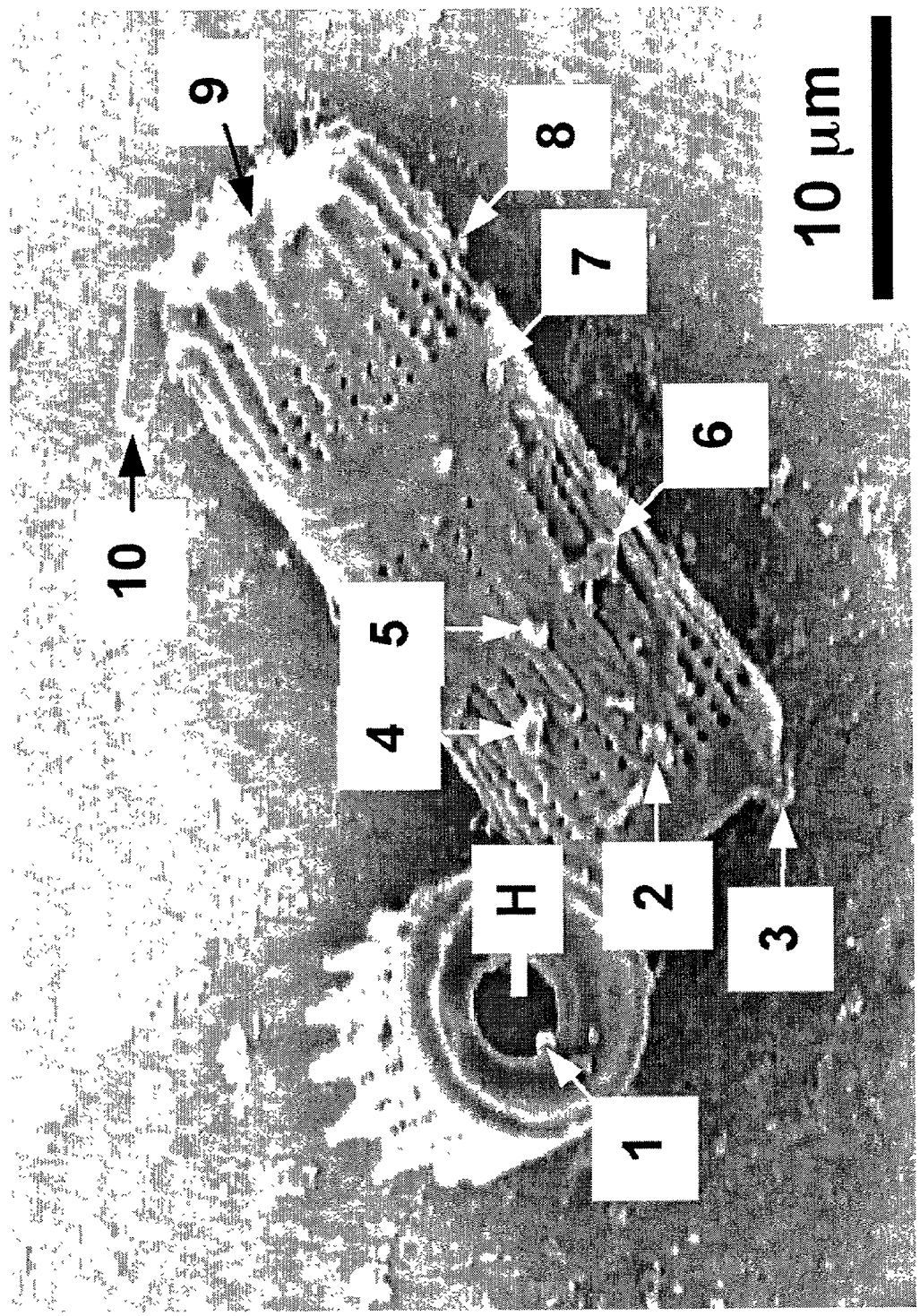
FIG. 4A is a secondary electron image of frustules of a naturally-occurring Aulacoseira diatom in accordance with one embodiment of the present invention.
Figure 4B:
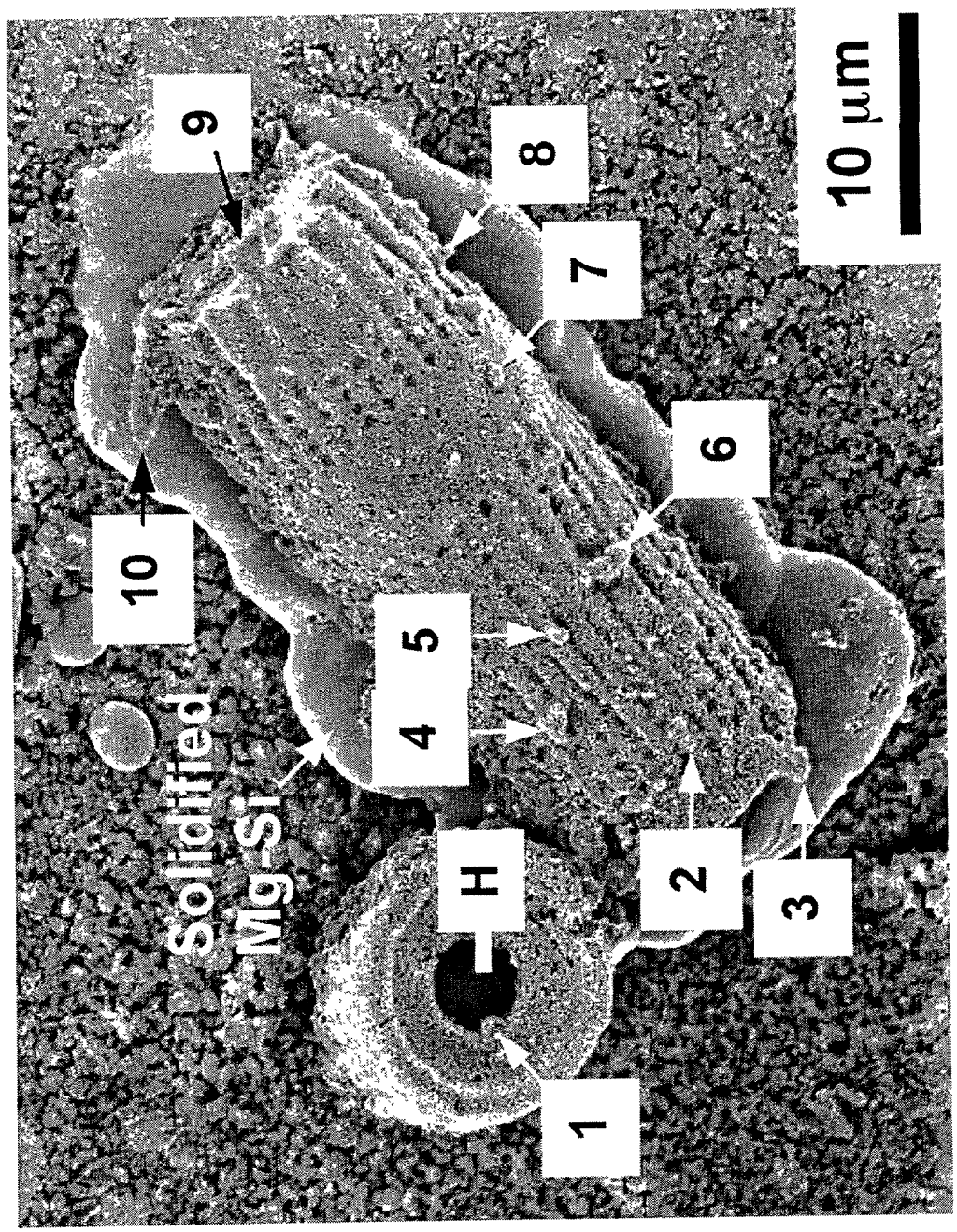
FIG. 4B is a secondary electron image of frustules of a naturally-occurring Aulacoseira diatom after reaction with gaseous magnesium for 4 hours at 900° C. in accordance with one embodiment of the present invention.
Figure 5:
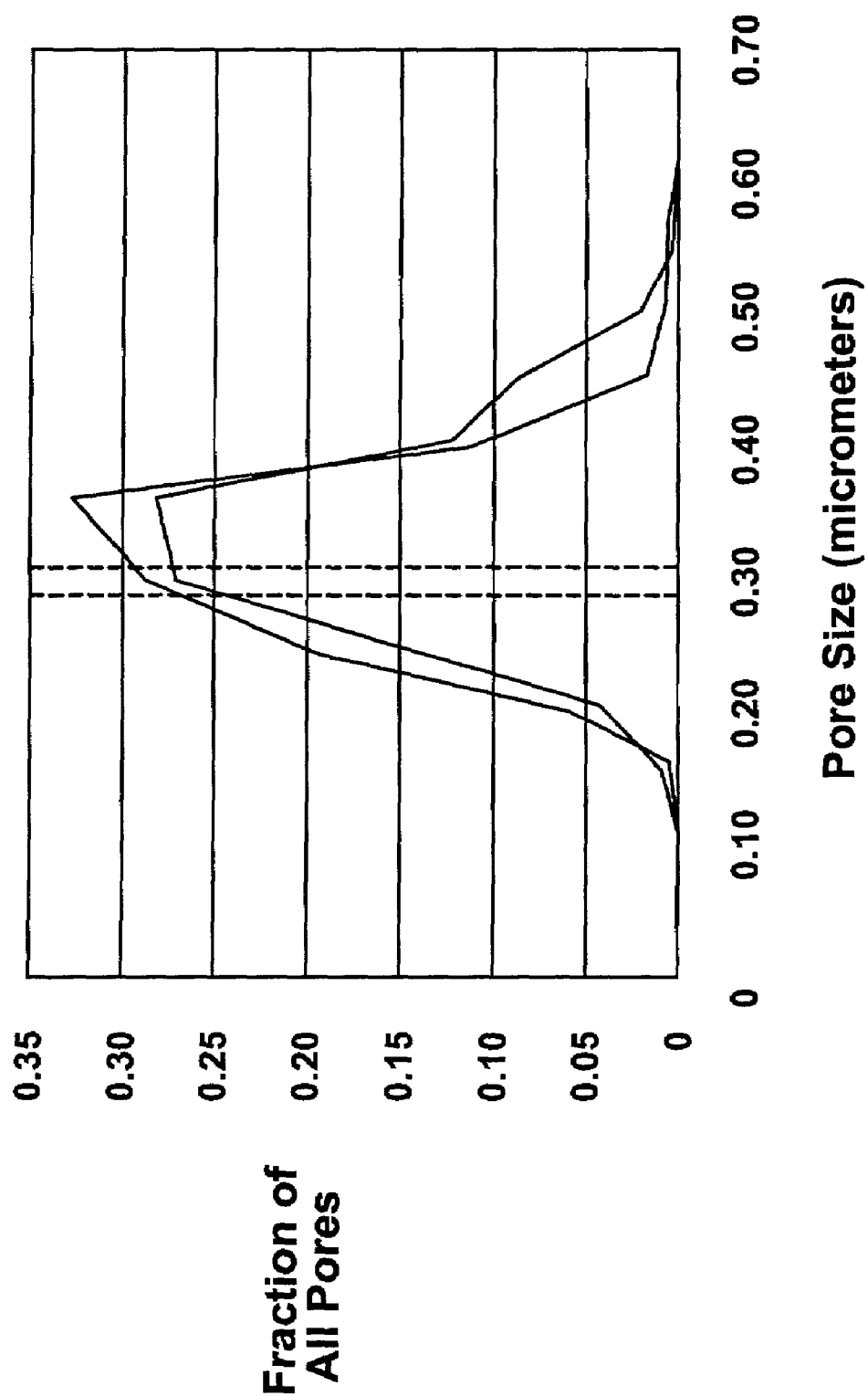
FIG. 5 is a graph of the distributions of the sizes of pores on the walls of the frustules of a naturally-occurring Aulacoseira diatom before and after reaction with gaseous magnesium in accordance with one embodiment of the present invention.

The reacted Aulacoseira frustules shown in FIGS. 3A and 3B were not produced from exactly the same frustules as shown in FIGS. 2A–2C. Secondary electron images of the same Aulacoseira frustules before and after reaction with Mg(g) for 4 hours at 900° C. are shown in FIGS. 4A and 4B, respectively. In both FIGS. 4A and 4B, 10 protuberances (along with the hole at the frustule end, labeled H) were identified. Comparison of FIGS. 4A and 4B reveals that the frustule shapes, surface features (e.g., the 10 protuberances), and fine pores were precisely retained after reaction with Mg(g). Image analyses were conducted to evaluate the changes in the sizes of the pores running along the walls of the frustules as a result of reaction with Mg(g). A plot of the size distributions of the pores before and after reaction with Mg(g) for 4 hours at 900° C. is shown in FIG. 5. There was no significant difference in the observed distributions of the pore sizes (i.e., the average pore size remained 300±73 nanometers before and after reaction; the average pore sizes before and after reaction are indicated by the vertical dashed lines in FIG. 5).

Figure 6:
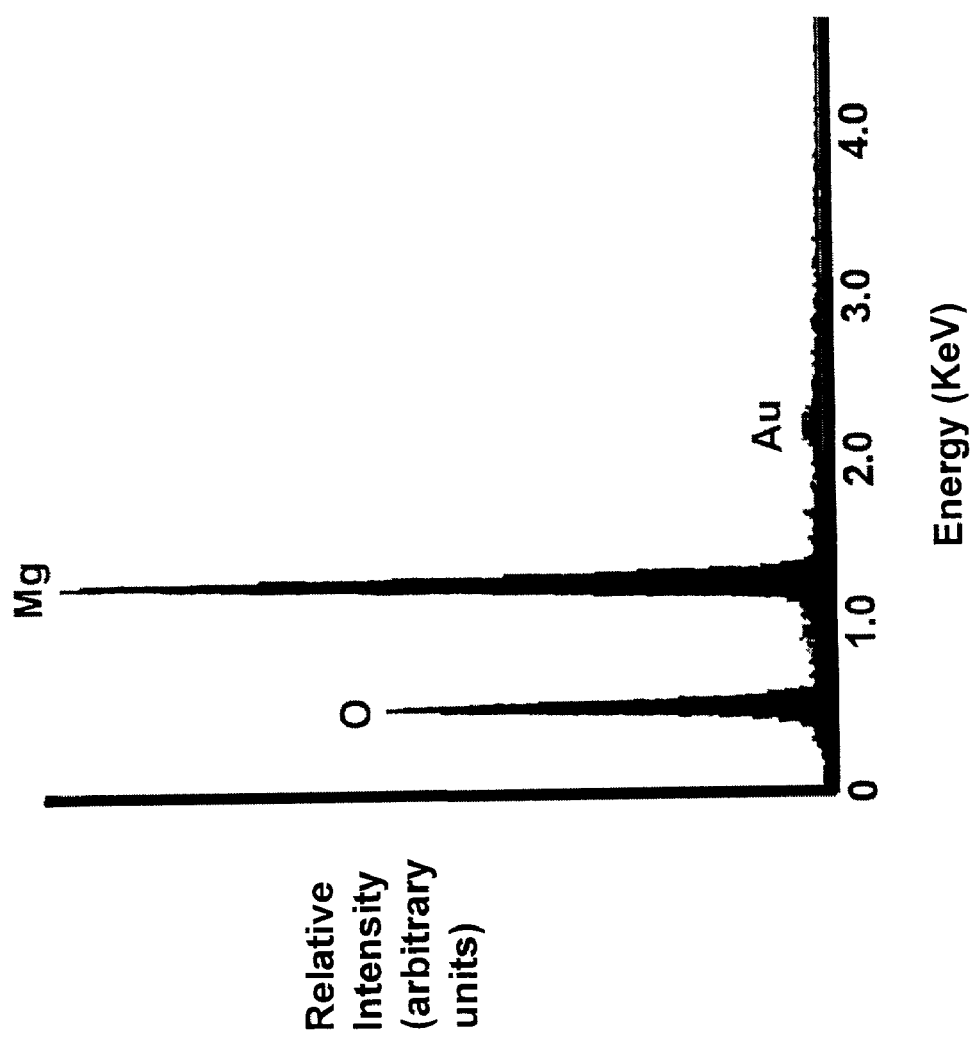
FIG. 6 is an energy dispersive x-ray spectrum obtained from the frustule of a naturally-occurring Aulacoseira diatom after reaction with gaseous magnesium in accordance with one embodiment of the present invention.

An energy-dispersive x-ray (EDX) pattern obtained from one of the reacted diatom frustules in FIG. 4B is shown in FIG. 6. Peaks for Mg and O were observed (note: the peak for gold, Au, in FIG. 6 was a result of coating the reacted diatom frustule with gold to avoid electrical charging of the specimen surface). The presence of magnesium and oxygen, and the absence of silicon, in such EDX analyses were consistent with the complete conversion of the $SiO_2$ in the Aulacoseira frustules into MgO within 4 hours of exposure to Mg(g) at 900° C. EDX analyses conducted with transmission electron microscopy of electron-transparent cross-sections of Aulacoseira frustules after exposure to Mg(g) for 4 hours at 900° C. also revealed the presence of MgO and absence of residual $SiO_2$.

Figure 7:
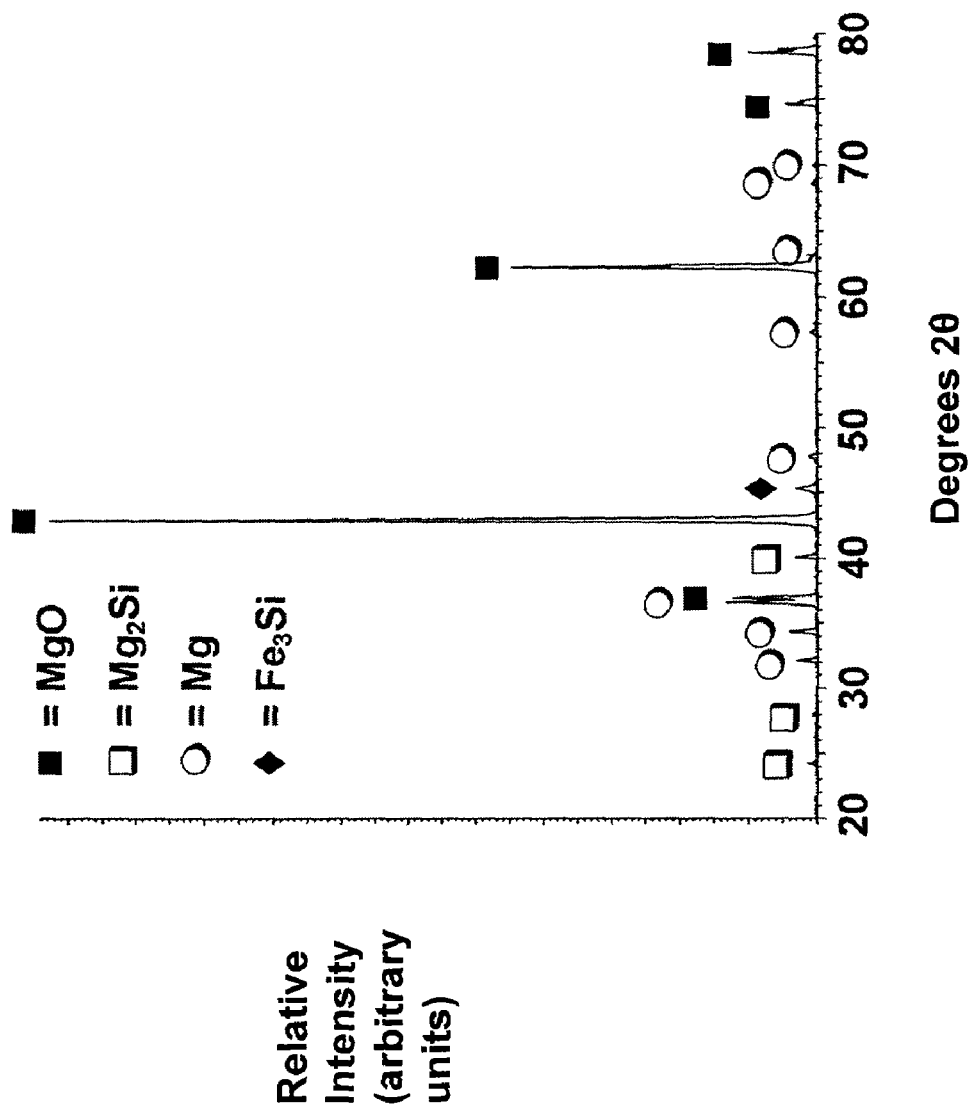
FIG. 7 is an x-ray diffraction pattern obtained from frustules of a naturally-occurring Aulacoseira diatom after reaction with gaseous magnesium for 4 hours at 900° C. in accordance with one embodiment of the present invention.

An x-ray diffraction pattern obtained from the reacted diatomaceous earth powder (reaction with Mg(g) for 4 hours at 900° C.) is shown in FIG. 7. This x-ray diffraction pattern reveals strong peaks for MgO and relatively weak peaks for $Mg_2Si$, Mg, and $Fe_3Si$. Peaks for crystalline polymorphs of silica (quartz, cristobalite, tridymite) were not detected. The presence of small amounts of $Mg_2Si$ and Mg in the XRD pattern of FIG. 7 were consistent with the Mg-Si phase diagram, which indicates that a Mg-rich, Mg—Si liquid should crystallize into $Mg_2Si$ and Mg upon solidification (Bulletin of Alloy Phase Diagrams, Volume 5, Number 6, page 584, 1984). The solidified Mg—Si liquid can be seen below the reacted Aulacoseira frustules in FIG. 4B. This Mg—Si liquid formed upon continued reaction of Si (generated upon reduction of $SiO_2$) with Mg(g). The presence of a weak diffraction peak for $Fe_3Si$ in FIG. 7 is a result of the reaction of the silicon in the Mg—Si liquid with the iron in the underlying steel substrate.

These images and analyses prove that fluid/solid displacement reactions may be used to completely convert biologically-derived silica microtemplates (i.e., silica-based diatom frustules) into microcomponents comprised of oxides of a different chemical composition than silica, while retaining the shapes and surface features of the starting silica microtemplates (diatom frustules).

EXAMPLE 2

Figure 8:
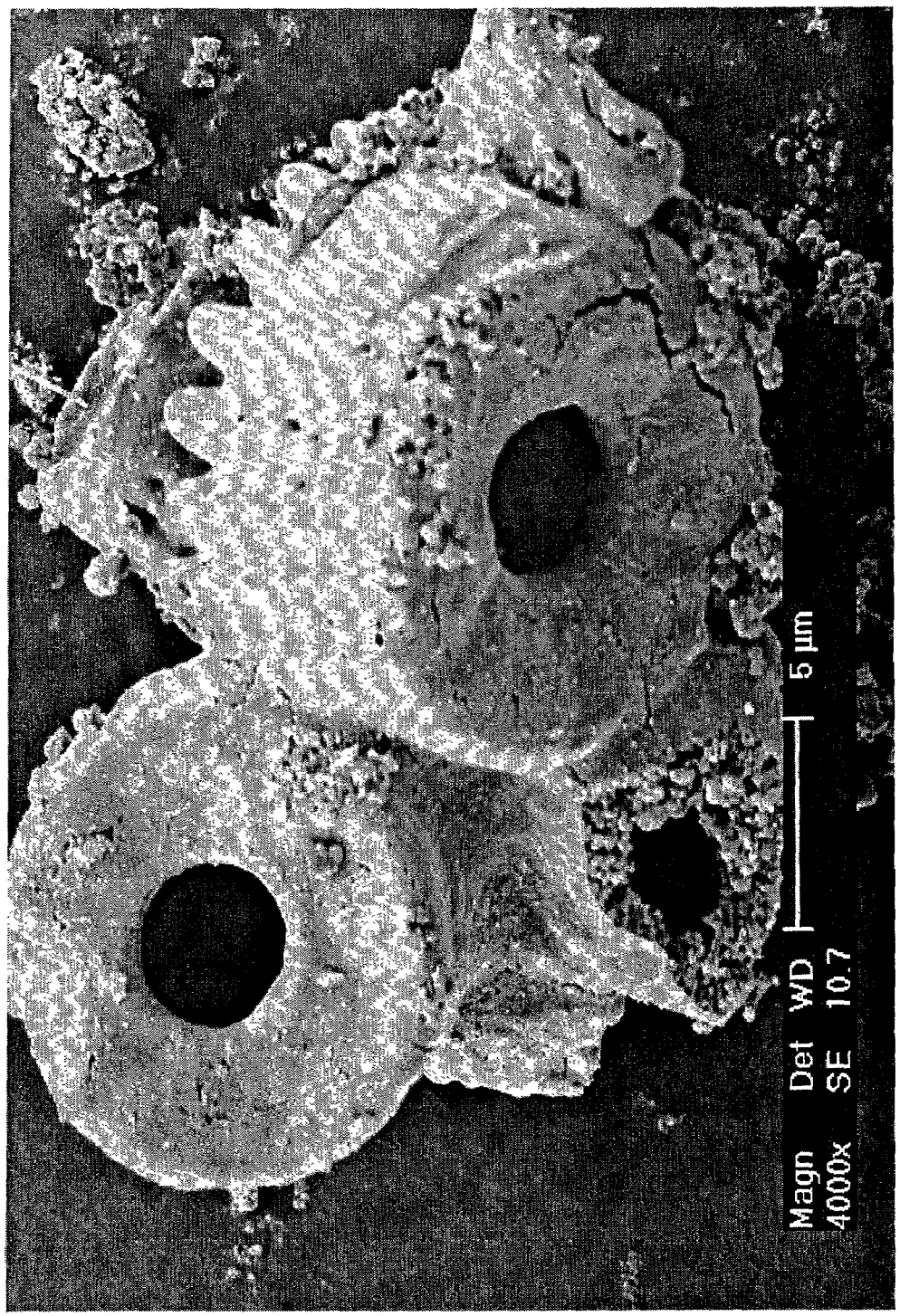
FIG. 8 is a secondary electron image of a cluster of frustules of naturally-occurring Aulacoseira diatoms after reaction with gaseous calcium for 4 hours at 1100° C. in accordance with one embodiment of the present invention.

Conversion of a $SiO_2$ Frustule into a $CaO/SiO_2$-bearing Composite Microcomponent with Preservation of the Starting Frustule Shape The Aulacoseira diatom frustules obtained from a local vendor were placed in a ceramic crucible and then heated to 600° C. for a total of 8 hours in air, in order to burn away any residual organic material. The resulting powder was then sealed inside a steel tube (in a manner similar to example 1) along with some solid magnesium. After sealing the tube, the assembly was heated in an inert atmosphere (Ar) tube furnace for 4 hours at 1100° C. After this heat treatment, the steel tube was cut open and the reacted diatomaceous earth powder was removed. An x-ray diffraction pattern of the reacted powder revealed significant peaks for $SiO_2$ and CaO, which indicated that appreciable conversion of the silica diatom frustule into CaO had occurred within 4 hours at 1100° C. A secondary electron image of the partially-converted Aulacoseira diatom frustule is shown in FIG. 8 below. This image reveals several frustules present within a cluster. Although some of the partially-reacted frustules exhibited cracking, the general shapes of the Aulacoseira diatom frustules were retained after partial conversion of the silica into calcium oxide. This example indicates that shaped microcomponents consisting of composites of multiple oxides can be produced by the partial conversion of biologically-derived microtemplates via a fluid/solid displacement reaction. These converted microcomponents retained the shapes of the starting, biologically-derived microtemplates.

EXAMPLE 3

Figure 9A:
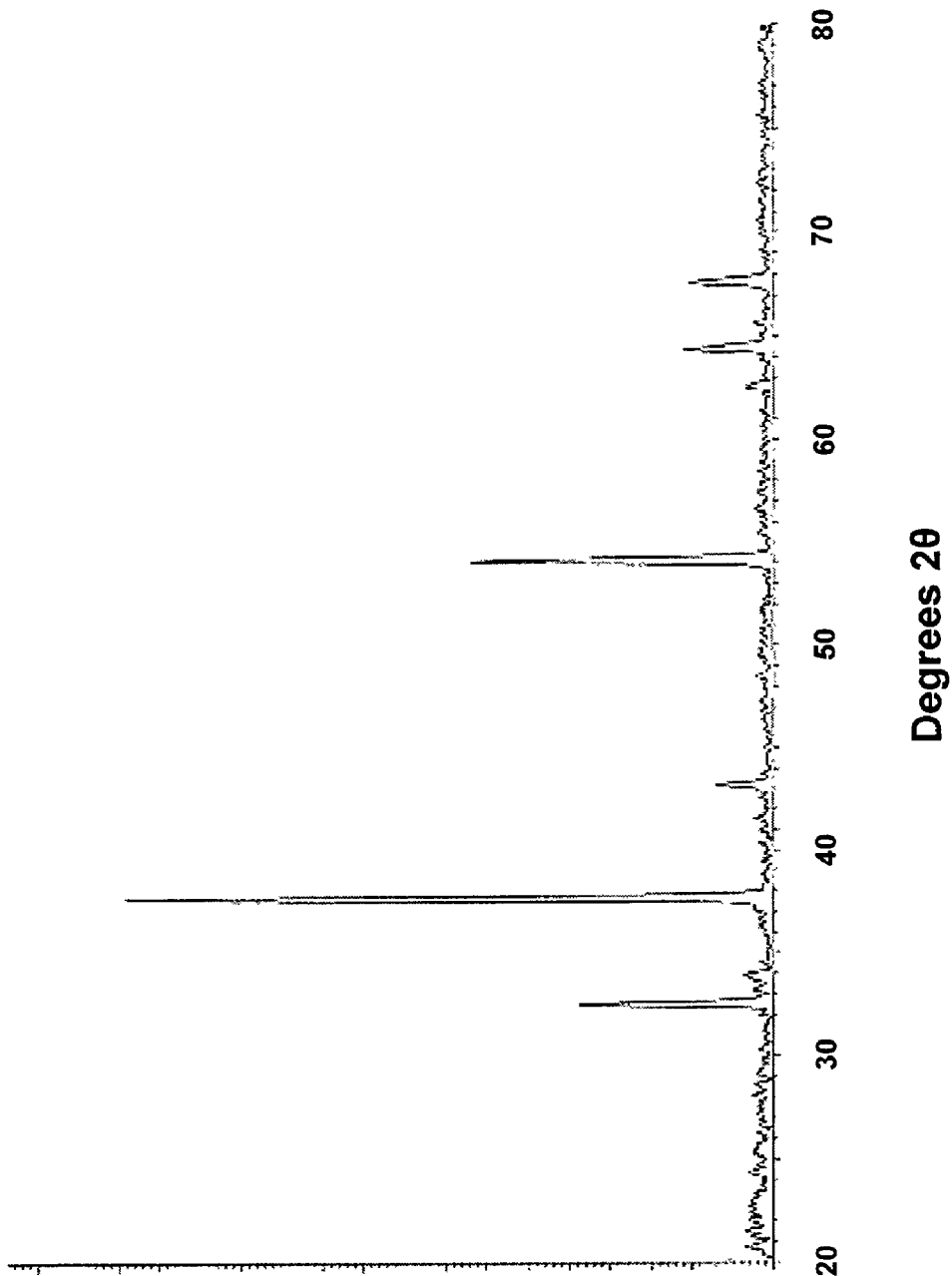
FIG. 9A is an x-ray diffraction pattern obtained from the frustule of a naturally-occurring Aulacoseira diatom after reaction with gaseous magnesium for 4 hours at 900° C. and then with gaseous calcium for 4 hours at 1100° C. in accordance with one embodiment of the present invention.
Figure 9B:
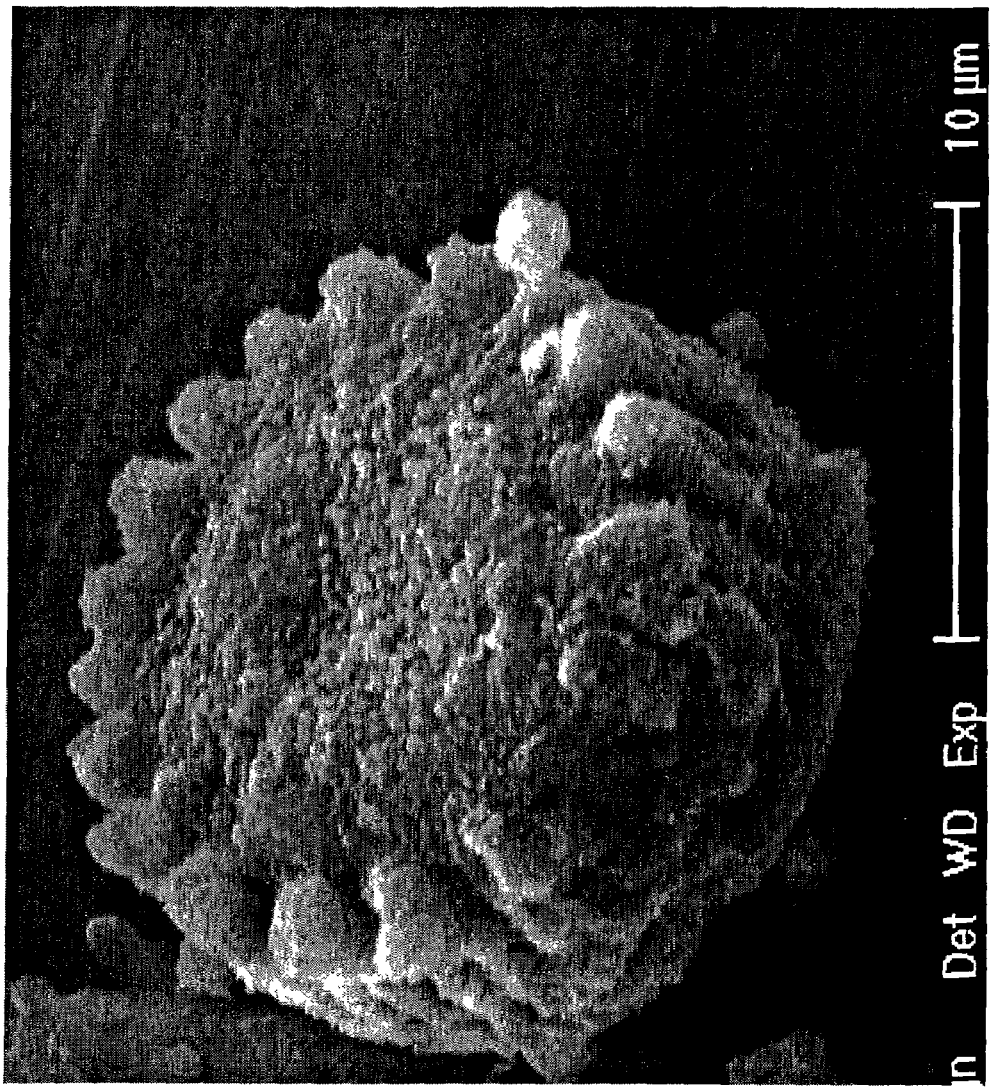
FIG. 9B is a secondary electron image of a frustule of a naturally-occurring Aulacoseira diatom after reaction with gaseous magnesium for 4 hours at 900° C. and then with gaseous calcium for 4 hours at 1100° C. in accordance with one embodiment of the present invention.
Figure 9C:
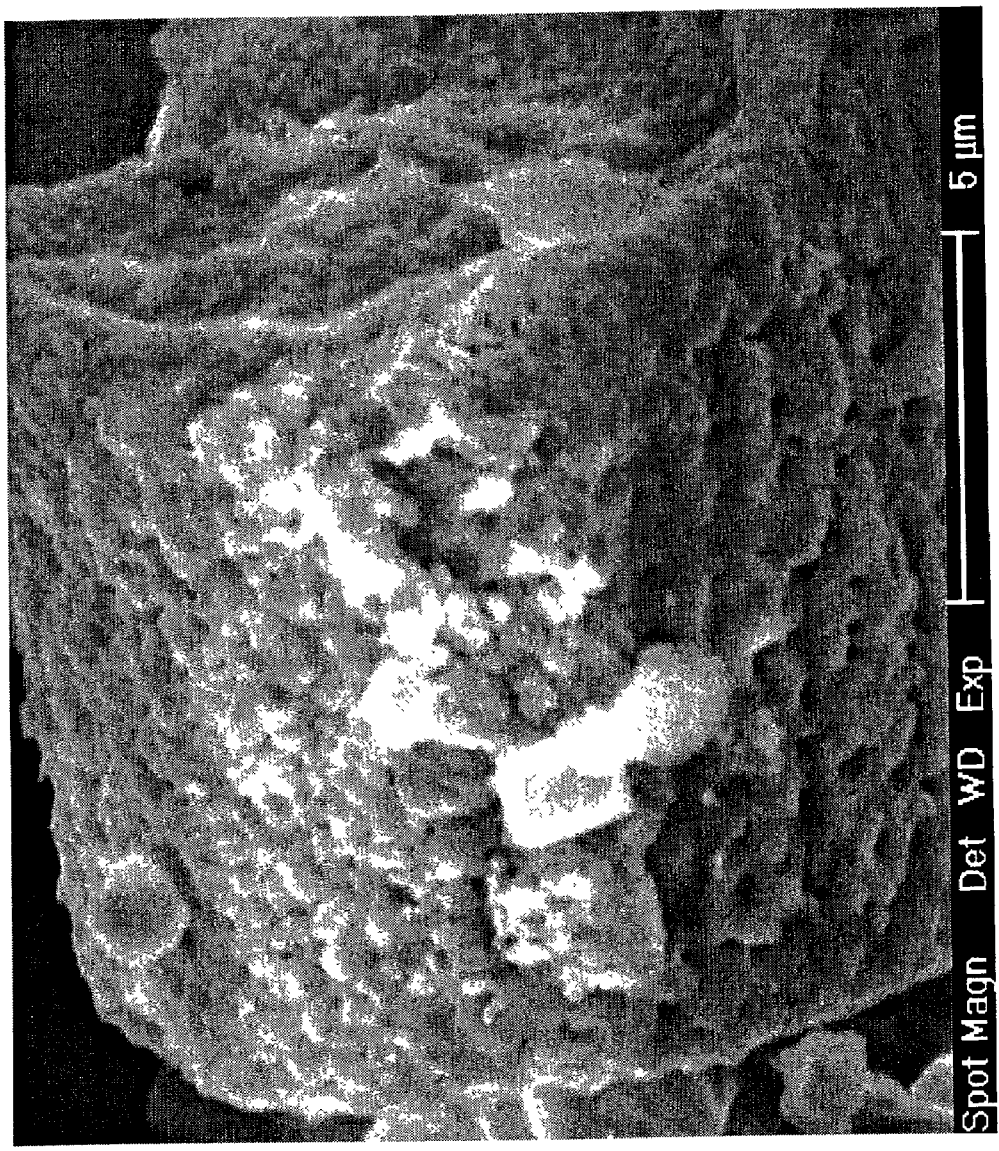
FIG. 9C is a secondary electron image of a frustule of a naturally-occurring Aulacoseira diatom after reaction with gaseous magnesium for 4 hours at 900° C. and then with gaseous calcium for 4 hours at 1100° C. in accordance with one embodiment of the present invention.

Conversion of a $SiO_2$ Frustule into a CaO/MgO-bearing Composite Microcomponent with Preservation of the Starting Frustule Shape The Aulacoseira diatom frustules obtained from a local vendor were placed in a ceramic crucible and then heated to 600° C. for a total of 8 hours in air, in order to burn away any residual organic material. The resulting powder was then sealed inside a steel tube (in a manner similar to example 1) along with some solid magnesium. After sealing the tube, the assembly was heated in an inert atmosphere (Ar) tube furnace for 4 hours at 900° C. After this heat treatment, the steel tube was cut open and the reacted diatomaceous earth powder was removed. The powder was then resealed into a new steel tube along with some solid calcium. The assembly was then heated in an inert atmosphere (Ar) tube furnace for 4 hours at 1100° C. After this heat treatment, the steel tube was cut open and the reacted diatomaceous earth powder was removed. An x-ray diffraction pattern of the reacted powder is shown in FIG. 9A. This XRD pattern exhibited predominant peaks for CaO, along with smaller peaks for MgO. A small peak for $CaSi_2$ was also detected. Secondary electron images of converted Aulacoseira diatom frustules are shown in FIGS. 9B and 9C. These images reveal polycrystalline CaO/MgO composite frustules that have retained the general shapes of the starting Aulacoseira diatom frustules. This example indicates that a series of fluid/solid displacement reactions (i.e., conversion into MgO by the reaction of diatom $SiO_2$ with Mg(g), followed by conversion into CaO by the reaction of MgO with Ca(g)) can be used to produce microcomponents comprised of multiple oxides other than the oxide in the starting, biologically-derived microtemplate. These composite microcomponents retained the shapes of the starting, biologically-derived microtemplates.

EXAMPLE 4

Figure 10:
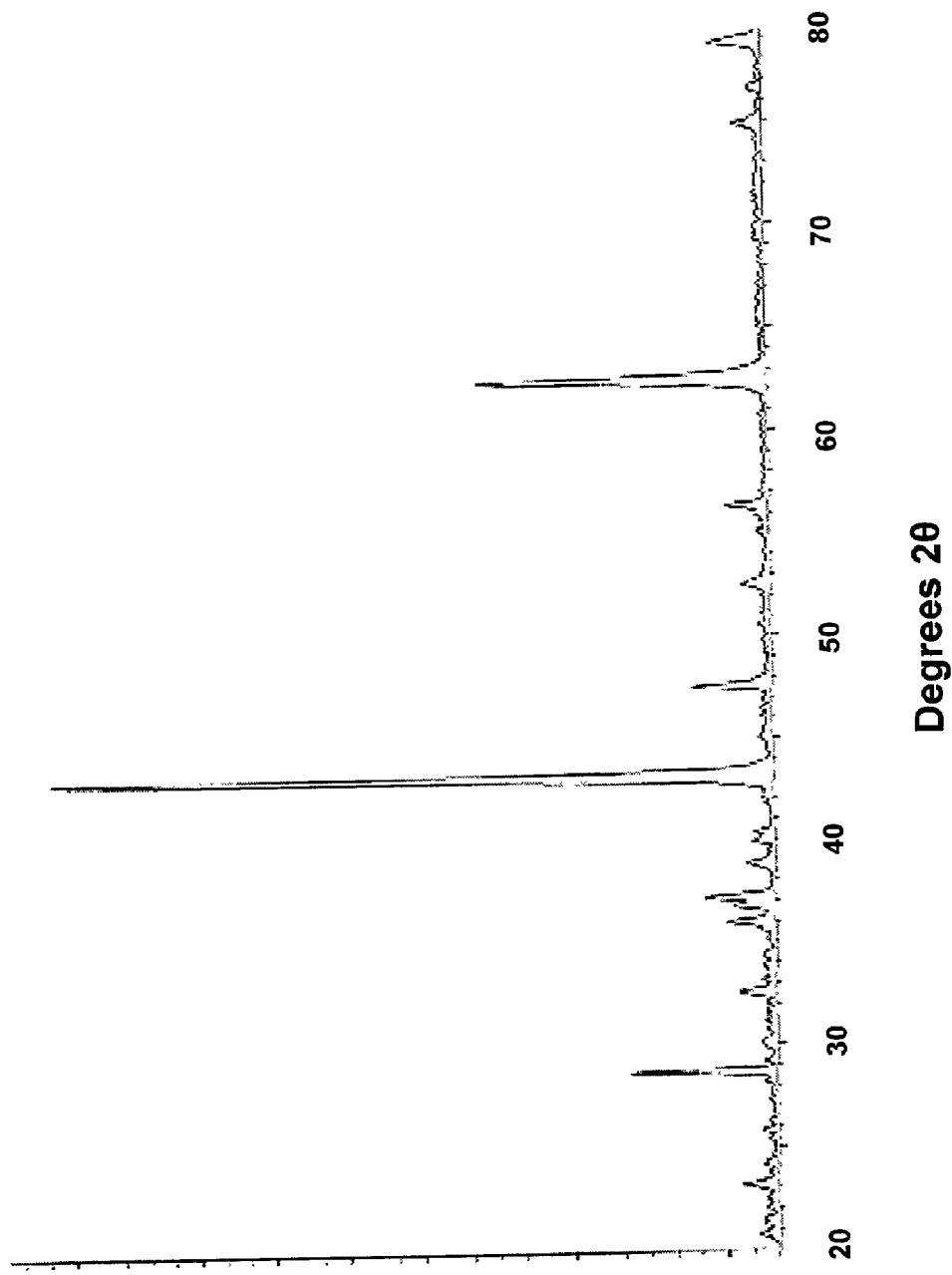
FIG. 10 is an x-ray diffraction pattern obtained from the frustule of a naturally-occurring Aulacoseira diatom after reaction with gaseous magnesium for 4 hours at 900° C. and then annealing for 4 hours at 1100° C. in accordance with one embodiment of the present invention.

Conversion of a $SiO_2$ Frustule into a $MqO/Mg_2SiO_4$-bearing Composite Microcomponent with Preservation of the Starting Frustule Shape The Aulacoseira diatom frustules obtained from a local vendor were placed in a ceramic crucible and then heated to 600° C. for a total of 8 hours in air, in order to burn away any residual organic material. The resulting powder was then sealed inside a steel tube (in a manner similar to example 1) along with some solid magnesium. After sealing the tube, the assembly was heated in an inert atmosphere (Ar) tube furnace for 4 hours at 900° C. After this heat treatment, the steel tube was cut open and the reacted diatomaceous earth powder was removed. The reacted diatomaceous earth powder was placed in a ceramic crucible and then heated in an inert atmosphere (Ar) tube furnace for 4 hours at 1100° C. An x-ray diffraction pattern of the reacted powder is shown in FIG. 10. This XRD pattern exhibited predominant peaks for MgO, along with smaller peaks for $Mg_2SiO_4$ and Si. This example indicates that a series of reactions involving a gas/solid displacement reaction (i.e., partial conversion into MgO by the reaction of $SiO_2$ with Mg(g)) and an additive solid/solid reaction (i.e., reaction of MgO with $SiO_2$ to produce $Mg_2SiO_4$) can be used to produce microcomponents comprised of multiple oxides, including multicomponent oxide compounds (i.e., $Mg_2SiO_4$), other than the oxide in the starting, biologically-derived microtemplate. These composite microcomponents retained the shapes of the starting, biologically-derived microtemplates.

EXAMPLE 5

Figure 11A:
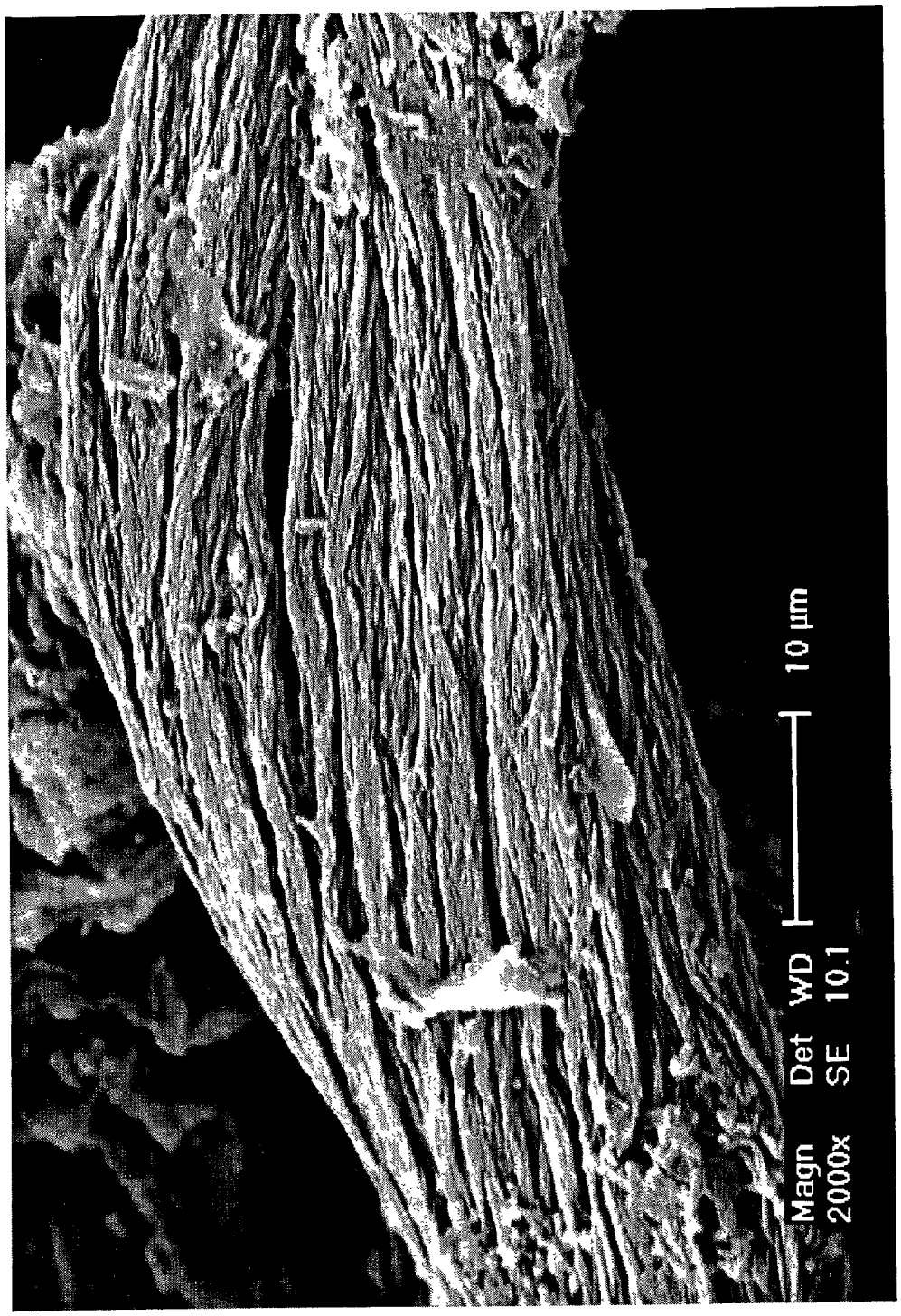
FIG. 11A is a secondary electron image of a biocatalyzed silica multifilamentary microtemplate produced by passing a silaffin-derived biocatalyst in a crosscurrent (shear flow) pattern against an opposing stream of a silicic acid solution in accordance with one embodiment of the present invention.
Figure 11B:
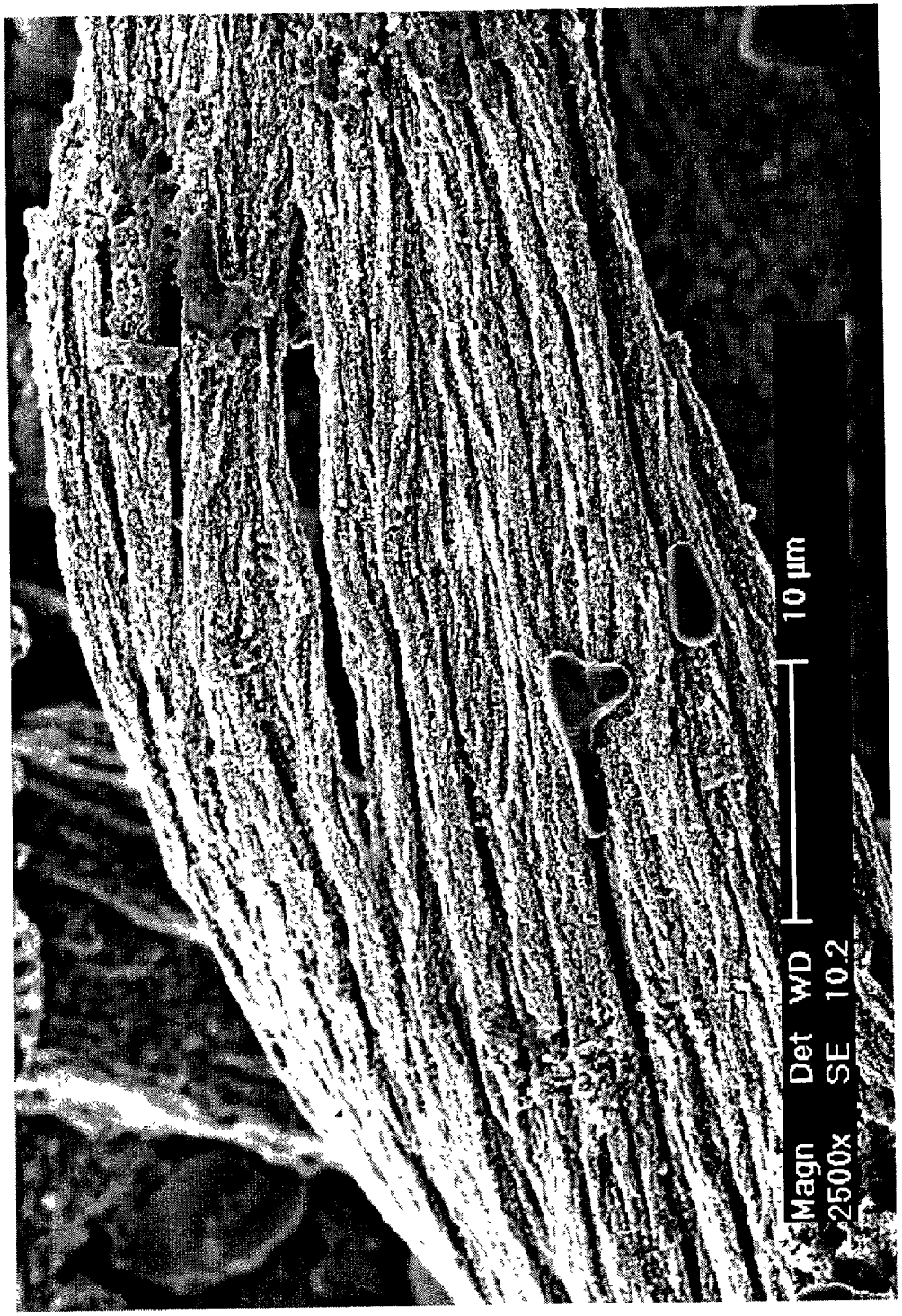
FIG. 11B is a secondary electron image of the biocatalyzed silica multifilamentary microtemplate from FIG. 11A after reaction with gaseous magnesium for 4 hours at 900° C. in accordance with one embodiment of the present invention.

Conversion of a Biocatalyzed $SiO_2$ Microtemplate into MgO with Preservation of Shape and Fine Features A biocatalyzed, multifilamentary silica microtemplate was obtained from Dr. Morley O. Stone (Biotechnology Project Leader, Air Force Research Laboratory, Wright Patterson Air Force Base, Ohio). A secondary electron image of this biocatalyzed microtemplate is shown in FIG. 11A. This structure was produced by passing a silaffin-derived biocatalyst in a crossflow (shear flow) pattern against an opposing stream of a silicic acid solution. The biocatalyst was a short 19-amino-acid R5 peptide unit (SSKKSGSYSG-SKGSKRRIL) of the silaffin-1 precursor polypeptide from the diatom *Cylindrotheca fusiformis*. (see Brott, et al., Nature, Volume 413, pages 291-293, Sep. 20, 2001). This multifilamentary silica microtemplate was placed in a ceramic crucible and then heated to 600° C. for a total of 8 hours in air, in order to burn away any residual organic material. The resulting microtemplate was then placed on a steel substrate and sealed inside a steel tube (in a manner similar to example 1) along with some solid magnesium. After sealing the tube, the assembly was heated in an inert atmosphere (Ar) tube furnace for 4 hours at 900° C. After this heat treatment, the tube was cut open and the specimen was removed. X-ray diffraction analyses indicated that this heat treatment resulted in conversion of the $SiO_2$ into MgO. A secondary electron image of the reacted microtemplate is shown in FIG. 11B. The converted MgO microcomponent retained the shape, multifilamentary structure, and fine features (gaps, protuberances) of the starting, biocatalyzed $SiO_2$ microtemplate of FIG. 11A. This example demonstrates that a shaped, biocatalyzed microtemplate can be converted into a new oxide composition via a fluid/solid displacement reaction while retaining the same shape and fine features.

The preferred embodiments herein disclosed are not intended to be exhaustive or to unnecessarily limit the scope of the invention. The preferred embodiments were chosen and described in order to explain the principles of the present invention so that others skilled in the art may practice the invention. Having shown and described preferred embodiments of the present invention, it will be within the ability of one of ordinary skill in the art to make alterations or modifications to the present invention, such as through the substitution of equivalent chemicals or through the use of equivalent process steps, so as to be able to practice the present invention without departing from its spirit as reflected in the appended claims, the text and teaching of which are hereby incorporated by reference herein. It is the intention, therefore, to limit the invention only as indicated by the scope of the claims and equivalents thereof. The text and teaching of the claims are hereby incorporated by references into the specification.

The invention claimed is:

1. A method for the production of a shaped microcomponent, comprising:
    a) providing at least one biologically-derived silica microtemplate having an original chemical composition and an original dimensional feature, wherein the at least one biologically-derived silica microtemplate is a frustule of a diatom species; and
    b) subjecting said at least one biologically-derived silica microtemplate to at least one chemical reaction so as to at least partially convert said at least one biologically-derived silica microtemplate into a shaped microcomponent comprising a solid oxide, wherein the at least one chemical reaction is selected from the group consisting of additive reaction, metathetic reaction, oxidation-reduction reaction, or combinations thereof; and wherein at least a portion of the shaped microcomponent has a different chemical composition than the biologically-derived silica microtemplate, but substantially the same dimensional feature as the biologically-derived silica microtemplate.

2. The method of claim 1, wherein said at least one biologically-derived microtemplate is a naturally-occurring microtemplate.

3. The method of claim 1, wherein said at least one biologically-derived microtemplate is a biologically-derived mineral containing article having a shape provided by nature.

4. The method of claim 1, wherein said at least one biologically-derived microtemplate is derived from a genetically altered organism that constructs said microtemplate having a dimensional feature different than a microtemplate produced by a non-altered organism of the same type as said genetically altered organism.

5. The method of claim 1, wherein said chemical reaction is an additive reaction of the following type:

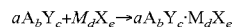

where $A_bY_c$ is a reactant, $M_dX_e$ is a constituent of the said at least one biologically-derived microtemplate, and $aA_bY_c \cdot M_dX_e$ is an ionically or covalently bonded solid reaction product that is a solid compound, a solid solution, or a solid mixture that is retained in the said shaped microcomponent; and wherein a, b, c, d, and e are stoichiometric coefficients.

6. The method of claim 5 wherein $aA_bY_c \cdot M_dX_e$ is selected from the group consisting of solid oxides, solid oxide compounds, oxide solid solutions, solid oxide mixtures, and mixtures thereof.

7. The method of claim 5 wherein $aA_bY_c \cdot M_dX_e$ is selected from the group consisting of silicon oxide-bearing compounds, silicon oxide-bearing solid solutions, silicon oxide-bearing mixtures, and mixtures thereof.

8. The method of claim 7 wherein said silicon oxide-bearing compound is selected from the group consisting of aluminosilicates, alkali silicates, alkaline earth silicates, alkali aluminosilicates, alkaline earth aluminosilicates, borosilicates, cadmium silicates, cobalt silicates, erbium silicates, iron silicates, lead silicates, manganese silicates, neodymium silicates, nickel silicates, yttrium silicates, ytterbium silicates, zinc silicates, zircon, and mixtures thereof.

9. The method of claim 5 wherein $aA_bY_c \cdot M_dX_e$ is selected from the group consisting of calcium oxide-bearing compounds, calcium oxide-bearing solid solutions, calcium oxide-bearing mixtures, and mixtures thereof.

10. The method of claim 9 wherein said calcium oxide-bearing compound is selected from the group consisting of calcium alkali-silicates, calcium aluminates, calcium aluminosilicates, calcium alkali-aluminosilicates, calcium bismuthates, calcium borates, calcium cerates, calcium chromites, calcium cuprates, calcium ferrites, calcium gadolinium oxides, calcium gallates, calcium germanates, calcium hafnate, calcium manganates, calcium molybdates, calcium niobates, calcium phosphates, calcium hydroxyapatite, calcium plumbates, calcium silicates, calcium stannates, calcium sulfates, calcium tantalates, calcium titanates, calcium tungstates, calcium uranium oxides, calcium vanadates, calcium yttrium oxides, calcium zirconates, and mixtures thereof.

11. The method of claim 1, wherein said chemical reaction is a metathetic reaction of the following type:

$$aA_bY_c + M_dX_e \rightarrow aA_bX_{e/a} + M_dY_{ca}$$

where $A_bY_c$ is a reactant, $M_dX_e$ is a constituent of the said at least one biologically-derived microtemplate, $aA_bX_{e/a}$ is an onically or covalently bonded first solid reaction product that is a solid compound, a solid solution, or a solid mixture that is retained in the said shaped microcomponent, and $M_dY_{ca}$ is a second reaction product; and wherein a, b, c, d, e, e/a, and ca are stoichiometric coefficients.

12. The method of claim 11 wherein $aA_bX_{e/a}$ is selected from the group consisting of solid oxides, solid oxide compounds, oxide solid solutions, solid oxide mixtures, and mixtures thereof.

13. The method of claim 11 wherein $aA_bX_{e/a}$ is selected from the group consisting of Ethium oxide, beryllium oxide, boron oxide, sodium oxide, magnesium oxide, aluminum oxide, potassium oxide, calcium oxide, titanium oxide, vanadium oxide, chromium oxide, manganese oxide, iron oxide, cobaft oxide, nickel oxide, copper oxide, zinc oxide, germanium oxide, rubidium oxide, strontium oxide, yttrium oxide, zirconium oxide, niobium oxide, molybdenum oxide, cadmium oxide, indium oxide, tin oxide, antimony oxide, cesium oxide, barium oxide, lanthanum oxide, hafnium oxide, tantalum oxide, tungsten oxide, lead oxide, bismuth oxide, cerium oxide, neodymium oxide, samarium oxide, europium oxide, gadolinium oxide, dysprosium oxide, holmium oxide, erbium oxide, ytterbium oxide, and mixtures thereof.

14. The method of claim 1, wherein said chemical reaction is an oxidation-reduction reaction of the foliowing type:

$$yA + aM_xO_z \rightarrow yAO_{za/y} + axM$$

where A is a reactant $M_xO_z$ is an oxide constituent of the said at least one bioiogicaily-derived microteniplate, $yAO_{za/y}$ is an oxide first solid reaction product that le a solid compound, a solid solution, or a solid mixture that le retained in the said shaped microcomponent, and M is a second reaction product and wherein y, a, x, z, za/y, and ax are stoichiometric coefficlenta.

15. The method of claim 14 wherein $yAO_{za/y}$ is selected from the group consisting of solid oxides, solid oxide compounds, oxide solid solutions, solid oxide mixtures, and mixtures thereof.

16. The method of claim 14 wherein $yAO_{za/y}$ is selected from the group consisting of lithium oxide, beryllium oxide, magnesium oxide, aluminum oxide, calcium oxide, titanium oxide, strontium oxide, yttrium oxide,-zirconium oxide, antimony oxide, barium oxide, lanthanum oxide,hafnium oxide, cerium oxide, neodymium oxide, praseodymium oxide, samarium oxide, europium oxide, gadolinium oxide, dysprosium oxide,-holmium oxide, erbium oxide, thulium oxide, lutetium oxide, ytterbium oxide, and mixtures thereof.

17. The method of claim 1, wherein said chemical reaction involves at least two reactions selected from the group consisting of an additive reaction of the following type:

$$aA_bY_c + M_dX_e \rightarrow aA_bY_c \cdot M_dX_e$$

where $A_bY_c$ is a reactant, $M_dX_e$ is a constituent of the said at least one biologically-derived microtemplate, and $aA_bY_c \cdot M_dX_e$ is an ionically or covalently bonded solid reaction product that is a solid compound, a solid solution, or a solid mixture that is retained in the said shaped microcomponent; and wherein a, b, c, d, and e are stoichiometric coefficients; a metathetic reaction of the following type:

$$aA_bY_c + M_dX_e \rightarrow aA_bX_{e/a} + M_dY_{ca}$$

where $A_bY_c$ is a reactant, $M_dX_e$ is a constituent of the said at least one biologically-derived microtemplate, $aA_bX_{e/a}$ is an ionically or covalently bonded first solid reaction product that is a solid compound, a solid solution, or a solid mixture that is retained in the said shaped microcomponent, and MdYca is a second reaction product; and wherein a, b, c, d, e, e/a, and ca are stoichiometric coefficients; and an oxidation-reduction reaction of the following type:

$$yA + aM_xO_z \rightarrow yAO_{za/y} + axM$$

where A is a reactant, $M_xO_z$ is an oxide constituent of the said at least one biologically-derived microtemplate, $yAO_{za/y}$ is an oxide first solid reaction product that is a solid compound, a solid solution, or a solid mixture that is retained in the said shaped microcomponent, and M is a second reaction product; and wherein y, a, x, z, zaly, and ax are stoichiometric coefficients; and combinations thereof.

18. The method of claim 1, wherein said shaped microcomponent defines a cavity wherein said cavity is provided with at least one substance not native to said biologically-derived microtemnlate.

19. The method of claim 18, wherein said at least one substance is a pharmaceutically active substance.

20. The method of claim 1 wherein said shaped microcomponent possesses a shape selected from the group consisting of a solid microcylinder, a microtube, a solid microbar, a hollow microbar, a solid microsphere, a hollow microsphere, a solid microdisk, a hollow microdisk, a microwheel, a microgear, a microrotor, a microplate, a microtetrahedron, a microwedge, a microtetrakaidecahedron, a microspring, a microspiral, a microlever, a microcantilever, a solid microcone, a microfunnel, a microhoneycomb, a micromesh, a solid microcube, a hollow microcube, a solid microfiber, a hollow microfiber, and combinations thereof.

21. The method of claim 1 wherein said shaped microcomponent possesses at least one dimensional feature that is less than 1 millimeter in size.

22. The method of claim 1 wherein said shaped microcomponent possesses at least one dimensional feature that is less than 100 microns in size.

23. The method of claim 1 wherein said shaped microcomponent possesses at least one dimensional feature that is less than 25 microns in size.

24. The method of claim 1 wherein said shaped microcomponent possesses at least one dimensional feature that is less than 10 microns in size.

25. The method of claim 1 wherein said shaped microcomponent possesses at least one dimensional feature that is less than 1 micron in size.

26. The method of claim 1 wherein said shaped microcomponent possesses at least one dimensional feature that is less than 100 nanometers in size.

27. The method of claim 1 wherein said shaped microcomponent possesses at least one dimensional feature that is less than 25 nanometers in size.

28. The method of claim 1 wherein said shaped microcomponent possesses at least one dimensional feature that is less than 10 nanometers in size.

* * * * *

UNITED STATES PATENT AND TRADEMARK OFFICE
CERTIFICATE OF CORRECTION

PATENT NO.        : 7,067,104 B2
APPLICATION NO. : 10/158,582
DATED             : June 27, 2006
INVENTOR(S)       : Sandhage It is certified that error appears in the above-identified patent and that said Letters Patent is hereby corrected as shown below:

Title page, (54), please delete "SHAPED MICROCOMPONENT VIA REACTIVE CONVERSION OF BIOLOGICALLY-DERIVED MICROTEMPLATES" and insert -- SHAPED MICROCOMPONENTS VIA REACTIVE CONVERSION OF BIOLOGICALLY-DERIVED MICROTEMPLATES --.

Title page (56), References Cited, OTHER PUBLICATIONS, please delete "Kröger, et al., Polycationic Peptides from Diatom Biosilica That Direct Silica Nanosphere Formation, Science, vol. 285, Nov. 5, 1999." and insert -- Kröger, et al., Polycationic Peptides from Diatom Biosilica That Direct Silica Nanosphere Formation, Science, vol. 286, Nov. 5, 1999. --.

Title page (56), References Cited, OTHER PUBLICATIONS, please insert -- PARKINSON et al., Beyond Micromachining: The Potential of Diatoms, Trends in Biotechnology, Vol. 17, No. 5, pp. 190-196, 1999 --.

Title page (56), References Cited, OTHER PUBLICATIONS, please insert -- KRÖGER, et al., Species-specific polyamines from diatoms control silica morphology, PNAS, Vol. 97, no. 26, 14133-14138, December 19, 2000 --.

In column 1, lines 1-4, please delete "SHAPED MICROCOMPONENT VIA REACTIVE CONVERSION OF BIOLOGICALLY-DERIVED MICROTEMPLATES" and insert -- SHAPED MICROCOMPONENTS VIA REACTIVE CONVERSION OF BIOLOGICALLY-DERIVED MICROTEMPLATES --.

In column 1, lines 52-53, please delete "micro-machining" and insert -- micromachining --.

In column 1, line 53, please delete "photolithographylchemical" and insert -- photolithography/chemical --.

In column 1, line 55, please delete "electronic" and insert -- electronic --.

In column 1, line 56, please delete "rapid" and insert -- rapid --.

In column 1, lines 60-61, please delete "$\{\geqq 600° C.\}$ greater than or eaual to 600° C." and insert -- greater than or equal to 600°C --.

In column 6, line 3, please delete "catalytlc" and insert -- catalytic --.

UNITED STATES PATENT AND TRADEMARK OFFICE
CERTIFICATE OF CORRECTION

PATENT NO. : 7,067,104 B2
APPLICATION NO. : 10/158,582
DATED : June 27, 2006
INVENTOR(S) : Sandhage It is certified that error appears in the above-identified patent and that said Letters Patent is hereby corrected as shown below:

In column 7, line 20, please delete "$aA_bY_c.M_dX_e$" and insert -- $aA_bY_c\cdot M_dX_e$ --.

In column 7, line 25, please delete "$A_bY_c.M_dX_e$" and insert -- $A_bY_c\cdot M_dX_e$" --.

In column 7, line 39, please delete "$3CaO.nP_xO_y(s)$" and insert -- $3CaO\cdot nP_xO_y(s)$ --.

In column 11, line 39, please delete "Into" and insert -- into --.

In column 11, line 58, please delete "little less than or eaual to 1%) " and insert -- little (less than or equal to 1%) --.

In column 14, line 65, please delete "$mCaO(s)+nP_xO_y(g)=>mCaO.nP_xO_y(s)$" and insert -- $mCaO(s) + nP_xO_y(g) => mCaO\cdot nP_xO_y(s)$ --.

In column 14, line 67, please delete "$mCaO(s)+nP_xO_y(g)+pH_2O(g) =>mCaO\cdot nP_xO_y\cdot pH_2O$" and insert -- $mCaO(s) + nP_xO_y(g) + pH_2O(g) => mCaO\cdot nP_xO_y\cdot pH_2O(s)$ --.

In column 15, line 2, please delete "$mCaO.nP_xO_y(s)$" and insert -- $mCaO\cdot nP_xO_y(s)$ --.

In column 15, line 3, please delete "$mCaO.nP_xO_y.pH_2O(s)$" and insert -- $mCaO\cdot nP_xO_y\cdot pH_2O(s)$ --

In column 15, line 5, please delete "$10CaO.6P_xO_y.2H_2O$" and insert -- $10caO\cdot 6P_xO_y\cdot 2H_2O$ --.

In column 18, line 6, please delete "60000" and insert -- 600°C --.

In column 20, line 52, please delete "$MqO/Mg_2SiO_4$-bearing" and insert -- $MgO/Mg_2SiO_4$-bearing --.

In column 22, lines 43-44, please delete "$aA_bY\text{-}_cM_dX_e$" and insert -- $aA_bY_c\cdot M_dX_e$ --.

In column 22, line 48, please delete "$aA_bY_c.M_dX_e$" and insert -- $aA_bY_c\cdot M_dX_e$ --.

In column 22, line 52, please delete "$aA_bY_c.M_dX_e$" and insert -- $aA_bY_c\cdot M_dX_e$ --.

In column 22, line 64, please delete "$aA_bY_c.M_dX_e$" and insert -- $aA_bY_c\cdot M_dX_e$ --.

In column 23, line 33, please delete "Ethium" and insert -- lithium --.

UNITED STATES PATENT AND TRADEMARK OFFICE
CERTIFICATE OF CORRECTION

PATENT NO.        : 7,067,104 B2
APPLICATION NO.   : 10/158,582
DATED             : June 27, 2006
INVENTOR(S)       : Sandhage It is certified that error appears in the above-identified patent and that said Letters Patent is hereby corrected as shown below:

In column 23, line 53, please delete " reactant $M_xO_z$" and insert -- reactant, $M_xO_z$ --.

In column 23, line 54, please delete "microteniplate" and insert -- microtemplate --.

In column 23, line 55, please delete "le" and insert -- is --.

In column 23, line 56, please delete "le" and insert -- is --.

In column 23, line 58, please delete "product and" and insert -- product; and --.

In column 23, line 59, please delete "coefficlenta" and insert -- coefficients --.

In column 24, line 1, please delete "hafnium" and insert -- -hafnium --.

In column 24, line 28, please delete "MdYca" and insert -- $M_dY_{ca}$ --.

In column 24, line 38, please delete "zaly" insert -- za/y --.

In column 24, line 43, please delete "microtemnlate" and insert -- microtemplate --.

Signed and Sealed this

Fifteenth Day of August, 2006

JON W. DUDAS
*Director of the United States Patent and Trademark Office*